United States Patent
Barnhill et al.

(10) Patent No.: US 11,602,257 B2
(45) Date of Patent: Mar. 14, 2023

(54) LOW-MOISTURE FOOTWEAR SANITIZING SYSTEM

(71) Applicant: Resurgent Health & Medical LLC, Golden, CO (US)

(72) Inventors: Paul R. Barnhill, Aurora, CO (US); Joshua V. Morsicato, Golden, CO (US)

(73) Assignee: Resurgent Health & Medical, LLC, Golden, CO (US)

( * ) Notice: Subject to any disclaimer, the term of this patent is extended or adjusted under 35 U.S.C. 154(b) by 1160 days.

(21) Appl. No.: 16/182,327

(22) Filed: Nov. 6, 2018

(65) Prior Publication Data

US 2019/0133414 A1 May 9, 2019

Related U.S. Application Data

(60) Provisional application No. 62/582,196, filed on Nov. 6, 2017, provisional application No. 62/582,199, filed on Nov. 6, 2017.

(51) Int. Cl.
| | |
|---|---|
| *A61L 2/18* | (2006.01) |
| *A47L 23/02* | (2006.01) |
| *A47L 23/26* | (2006.01) |
| *A47L 23/20* | (2006.01) |
| *A61L 2/26* | (2006.01) |

(52) U.S. Cl.
CPC ............... *A47L 23/02* (2013.01); *A47L 23/20* (2013.01); *A47L 23/26* (2013.01); *A61L 2/18* (2013.01); *A61L 2/26* (2013.01); *A61L 2202/14* (2013.01); *A61L 2202/15* (2013.01)

(58) Field of Classification Search
CPC .................................. A47L 23/02; A61L 2/18
See application file for complete search history.

(56) References Cited

U.S. PATENT DOCUMENTS

| | | | |
|---|---|---|---|
| 2,953,805 | A | 9/1960 | Sevenich |
| 9,457,383 | B1 | 10/2016 | Skerven |
| 2003/0029477 | A1 | 2/2003 | Dean |
| 2010/0296970 | A1 | 11/2010 | Trimarco et al. |
| 2012/0167325 | A1 | 7/2012 | Omidi |
| 2015/0096597 | A1 | 4/2015 | Patei et al. |

OTHER PUBLICATIONS

International Preliminary Report on Patentability for International (PCT) Application No. PCT/US2018/059459, dated May 22, 2020, 9 pages.
Cruz et al., "Study of moisture absorption characteristics of cotton terry towel fabrics," Procedia Engineering, 3rd International Conference on Natural Fibers; Advanced Materials for a Greener World, vol. 200, Jun. 21-23, 2017, pp. 389-398.
International Search Report and Written Opinion for International (PCT) Patent Appiication No. PCT/US2018/059459, dated Jan. 16, 2019, 19 pages.

*Primary Examiner* — Donald R Spamer
(74) *Attorney, Agent, or Firm* — Sheridan Ross P.C.

(57) ABSTRACT

The present disclosure describes a system for sanitizing footwear having a pan, two or more mats positioned in the pan, and a spraying system to spray disinfectant directly on one of the mats. One of the mats is an absorbent mat, which may be a reusable mat, a disposable pad, or a plurality of disposable pads. The other mat is a heavy mat and has one or more cutouts. The heavy mat is positioned on top of the absorbent mat. The system for sanitizing footwear is a quick and easy way to sanitize the soles of footwear in an environment that cannot have moisture or the tracking of water.

18 Claims, 12 Drawing Sheets

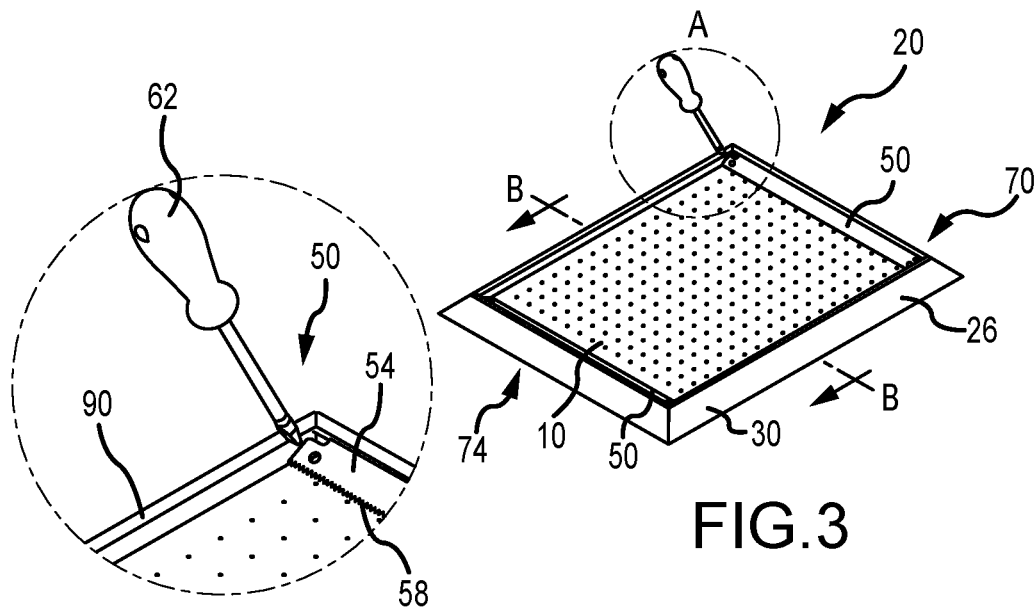
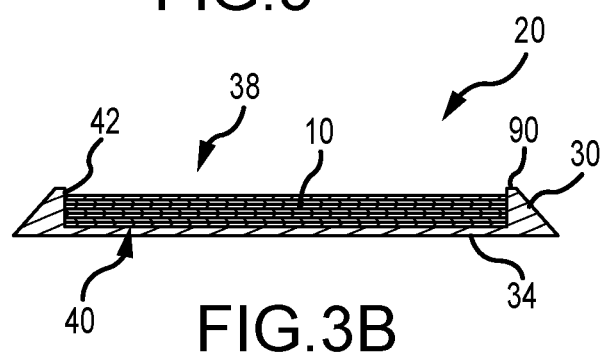
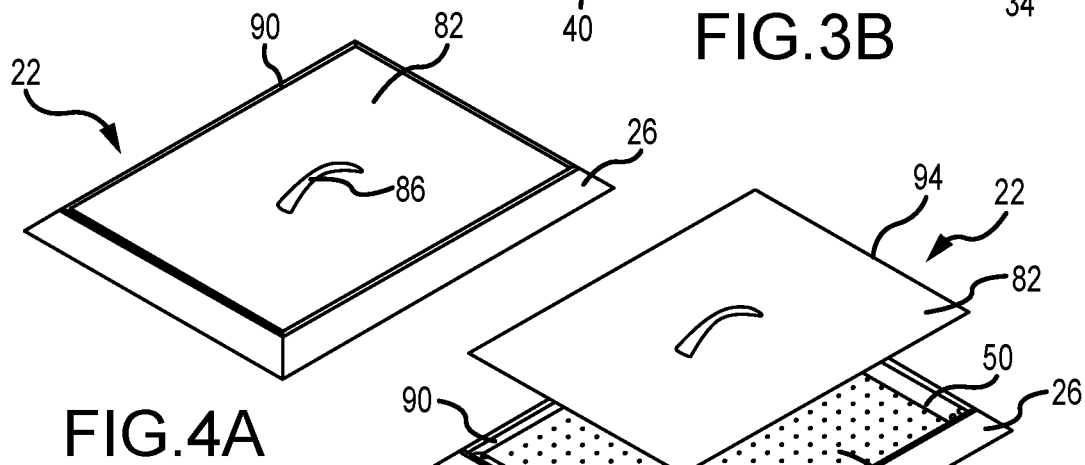
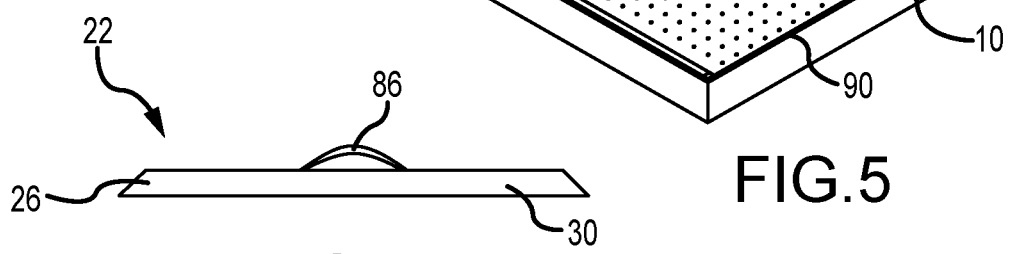

LOW-MOISTURE FOOTWEAR SANITIZING SYSTEM

CROSS REFERENCE TO RELATED APPLICATIONS

This application claims the benefit of and priority from U.S. Provisional Patent Application Ser. No. 62/582,199, filed Nov. 6, 2017, entitled "Low-Moisture Footwear Sanitizing Mat," and U.S. Provisional Patent Application Ser. No. 62/582,196, filed Nov. 6, 2017, entitled "Low-Moisture Footwear Sanitizing System," the entire disclosures of which are hereby expressly incorporated by reference in their entireties.

FIELD

The present disclosure is related generally to a system for sanitizing footwear in an environment that cannot have moisture or the tracking of water away from the sanitizing system.

BACKGROUND

Previous foot sanitation systems included wetted baths (e.g., boot dip water bath) having a pool of sanitizing liquid into which the user stepped to sanitize his footwear. Other prior systems included misters that sprayed the sanitizing liquid on the user's footwear. These systems were often messy and resulted in moisture or liquid being tracked by the user away from the system. The resulting puddles or moisture could create a slipping hazard or bring moisture into an environment that could not have the excess moisture present. Additionally, previous systems require regular cleaning and maintenance to keep the systems clean and functioning.

Accordingly, there exists a significant need for a footwear sanitation system that does not have standing liquid or track moisture or liquid into the area proximate to the footwear sanitation system. There also exists a need for a system with disposable portions such that cleaning and maintenance is minimized.

SUMMARY

These and other needs are addressed by the various embodiments and configurations of the present disclosure. The system of the present disclosure is a quick and easy way to sanitize the soles of footwear (e.g., street shoes, boots, or other shoes) in an environment that cannot have moisture or the tracking of water as would be typical with a traditional boot dip water bath system or a misting system.

It is one aspect of the present disclosure to provide a system with one or more mats for sanitizing footwear that does not require excessive moisture. For example, embodiments of the present disclosure do not track water, liquid, or moisture away from the sanitizing mat in the system. The terms "pad" and "mat" are used interchangeably herein.

Some embodiments of the system include an electromechanical system that sprays a sanitizing chemical to a predetermined location within a pan with an absorbable mat for the user to step on, wherein the sanitizer is then deposited to the soles of the user's shoes. In various embodiments, the sanitizing chemical is fast-drying.

Fast-drying refers to the time it takes the sanitizing chemical to dry or evaporate, i.e. how volatile the solution is. Volatility is quantified by the tendency of a substance to vaporize. Volatility is directly related to a substance's vapor pressure. At a given temperature, a substance with higher vapor pressure vaporizes more readily than a substance with a lower vapor pressure. Thus, the sanitizing chemical (also called the sanitizing solution herein) has a higher vapor pressure than water and a higher vapor pressure than typical footwear sanitizing solutions.

It is another aspect of the present disclosure to provide a system that quickly and easily sanitizes the soles of footwear. In some embodiments, the system is non-electronic and consists of a system sanitizer pan (also called a "tray" herein), a packet of pre-saturated or non-saturated absorbent pads, and a cover.

It is one aspect of the present disclosure to provide a system for sanitizing footwear with disposable pads that requires little cleaning and/or maintenance.

In one embodiment the pad is configured to fit in the sanitizing pan. Thus, the pad is sized and shaped similar to the pan. The pad may be held in place in the pan using a clamp, bar, weight, slot, or lever. In one embodiment, the mechanism to hold the pads in place is a spring-loaded bar. A screwdriver or other tool can be used to depress the bar, activate the spring, and lift the bar. The bar may be self-tightening on the lower pads after a top pad is removed for disposal.

In some embodiment, the pan includes one bar or other pad-retaining mechanism. In other embodiments, the pan includes two bars or other pad-retaining mechanisms positioned opposite one another in the pan. For example, one bar or other pad-retaining mechanism may be positioned in the front of the pan (proximate the user's toes when the user steps into the pan and onto the pad) and another bar or pad-retaining mechanism is positioned in the rear of the pan (proximate the user's heels when the user steps into the pan and onto the pad). Still other embodiments may have three or more pad-retaining mechanisms.

In one embodiment, the pan holds one or more absorbent pads in a cavity in the pan. The pads may be restrained in some manner such that they remain in the pan when a user steps onto the pad and off of the pad. The system may also include a cover that can be placed on the pan after each use, nightly, or between shifts depending on the frequency of the use of the system. The cover may be optional and provided for the pan for longer gaps between uses in order to prevent the pads from drying out.

In various embodiments, the absorbent pad is only one layer. In other embodiments, the pad is multiple layers, which may be the same material or different materials. The pad can be sold and packaged individually or packaged two or more pads per package. In some embodiments, the pads are pre-saturated. In alternative embodiments, the pads are dry and come with a container of liquid sanitizer to add to the pad(s) once the pad(s) is in position in the pan.

In some embodiments, the pads are disposable. In other embodiments, the pad is washable and reusable.

In some embodiments, the pads are packaged in various quantities, from one pad per package to any number of pads per package. Providing more than one absorbent pad in the system allows for the top pad to be replaced daily or multiple times per day as the pads wear or dry out. The quantity of pads per package or used in the system may be determined by the following: designed for daily change out may include 5-7 pads such that the package lasts one week depending on the length of the work week, designed for daily change out may include 10 pads such that the package lasts two five-day weeks, designed to change the pad multiple times per day at an average of two times per shift on a three-shift day may include 6 pads such that the package lasts one 24-hour day, designed to change the pad multiple times per day at an average of one time per shift on a four-shift day may include 4 pads such that the package lasts one 24-hour day, designed to change the pad multiple times per day at an average of one time per shift on a three-shift day may include 3 pads such that the package lasts one 24-hour day, designed to change the pad multiple times per day at an average of one time per shift on a two-shift day may include 2 pads such that the package lasts one 24-hour day, designed to change the pad multiple times per day at an average of two times per shift on a two-shift day may include 4 pads such that the package lasts one 24-hour day, designed to change the pad two times per day may include 10 pads such that the package lasts one five-day week, or any other desired combination.

In some embodiments, the pre-saturated absorbent pads are saturated with a sanitizing chemical and packaged in smaller quantities, i.e., 1-3 absorbent pads per package. The dry pads are typically packaged with 3-10 pads per package and come with a separate container of the sanitizing chemical that can be poured onto the pads once the pads have been installed in the pan. The sanitizing chemical for the dry pads can be in any size container from about a half pint (a cup) to about a gallon container.

In some embodiments, including the embodiments that employ one or more reusable mats, the sanitizing chemical can come in any size container from about a quart to a 55 gallon drum or a bag in a box.

Some embodiments of the mat system include a pan with an absorbent mat for the user to step on, where the mat is saturated with sanitizer and the sanitizer is deposited from the mat to the soles of the user's shoes.

In some embodiments, the system comprises two or three different mats. The first mat is the top mat, which is a heavy mat with cutouts for the shoe area. The top mat is typically reusable. The cutouts may be shoe-shaped, oval-shaped, or rectangular. The second mat (or middle mat) is the absorbent mat with the sanitizing chemical and is the mat on which the user actually stands. The second mat may be reusable and washable. Alternatively, the second mat may be disposable and replaced as necessary. The second mat is positioned below the first mat in the pan. The third mat is optional and is positioned below the second mat in the pan.

If the system is placed in front of an automated handwasher, the user can be washing his hands while standing in the pan with the mat or pad having the sanitizing chemical. In some embodiments, the handrail on the system is removable such that the sanitizing pan can be placed directly in front of an automated handwashing system.

The area where the user stands on the mat to have his shoe soles sanitized is called the "shoe area" herein.

In various embodiments, the sanitizing chemical is fast-drying. In one embodiment, the sanitizing chemical is a mixture of isopropyl alcohol and quaternary ammoniums. In some embodiments, the pads consist of mostly isopropyl alcohol. In some embodiments, the chemical is ready to use ("RTU") and does not require dilution. Other embodiments may require dilution with water and/or alcohol.

This system can be used as a standalone footwear sanitation system or can be used in conjunction with a handwashing system, which may be an automated system or a sink for manual handwashing.

In chemistry, absorption is a physical or chemical phenomenon or a process in which atoms, molecules, or ions enter some bulk phase: liquid or solid material. This is a different process from adsorption, since molecules undergoing absorption are taken up by the volume, not by the surface (as in the case for adsorption). A more general term is sorption, which covers absorption, adsorption, and ion exchange. Absorption is a condition in which something takes in another substance. The absorbent distributes the material it captures throughout the whole and adsorbent only distributes it through the surface. The IUPAC definition of absorption is "the process of one material (absorbate) being retained by another (absorbent); this may be the physical solution of a gas, liquid, or solid in a liquid, attachment of molecules of a gas, vapor, liquid, or dissolved substance to a solid surface by physical forces, etc."

If absorption is a physical process not accompanied by any other physical or chemical process, it usually follows the Nernst distribution law: the ratio of concentrations of some solute species in two bulk phases when it is in equilibrium and in contact is constant for a given solute and bulk phases. The value of constant $K_N$ depends on temperature and is called the partition coefficient. This equation is valid if concentrations are not too large and if the species "x" does not change its form in any of the two phases "1" or "2". If such molecule undergoes association or dissociation then this equation still describes the equilibrium between "x" in both phases, but only for the same form—concentrations of all remaining forms must be calculated by taking into account all the other equilibria. Absorption can be chemical (reactive) or physical (non-reactive).

"Absorptive" and "absorbent" may be be used interchangeably herein to describe a material, substance, or item that absorbs, i.e., has the power, capacity, or tendency to absorb.

If the pad material is a hydrophilic material and sorption happens via spontaneous imbibition, generally air is trapped in the pores of the pad. Air can fill 30-40% of the whole pore space. Even well connected parts of the pore space will contain air. Factors that prevent complete filling of the pore space are related the geometry of the pore space. Isolated voids will not be filled. Dead-end pores will also be responsible for air trapping. Further, liquid will spread throughout the fabric or material under capillary action. The level of wicking and liquid transportation in a fabric depends on pore sizes and their distribution. Liquid initially occupies small pores and then moves to larger pores.

The absorption capacity of a material may be referred to as the free swell values and given in grams of solution absorbed per gram of fiber ($g_{absorbed}/g_{fiber}$). The retention value of the material is given in grams of solution left in the fiber after a pressure (e.g., 20 mmHg) per gram of fiber ($g_{solution\ remaing}/g_{fiber}$).

The wetting phenomenon of textile structures involves numerous processes including immersion, capillary sorption, adhesion, and spreading. The pile length and areal density of the fabric affect the liquid absorption of the fabric. Liquid absorption tends to increase with an increase in the pile length (pile height) and increase in areal density. The percentage of liquid absorbed by fabrics with high loop density is higher than that of fabrics having lower loop density. The amount of liquid a material can absorb is also dependent on whether the fibers are twisted and how compact the fibers are and the material in general is. The more compact and/or twisted the fibers, the less liquid the material can absorb.

In some embodiments, the pad may be a continuous loop, similar to a belt on a treadmill. Thus, the pad belt moves around the belt base and pullies or rollers at each end. The advantage of a moving pad is that users will constantly step on different portions of the moving pad. Additionally, by forcing the user to step on and potentially walk on the moving surface, more sanitizing solution will be transferred to the soles of the user's shoes.

Alternative embodiments may include a tray with a pool of solution and a pad at the bottom of the tray/pool.

Additional embodiments may include the footwear sanitation system described herein (i.e., with a pan, pad, and cover) and also include a mister to disinfect additional surfaces of the user's shoes. Thus, after the user steps on the pad in the pan, the mister also sprays quick-drying sanitizing chemical on the upper portions of the user's shoes (i.e., the portions of the user's shoes other than the sole).

In one embodiment, a footwear sanitizing system is provided comprising: a pan with a bottom positioned on a floor and a cavity opening to an upper side of the pan opposite the bottom; a second mat positioned in the pan; a first mat positioned on top of the second mat within the cavity, wherein the first mat has at least one cutout extending through the first mat to the second mat such that the second mat is accessible through the at least one cutout in the first mat, wherein at least one of a liquid absorbency, permeability, and porosity of the second mat is greater than the first mat; a pump housing interconnected to the pan, the pump housing comprising a sensor, at least one nozzle, and a pump; a controller electrically interconnected to the pump and sensor; and a fluid container in fluid communication with the pump, wherein the fluid container contains a sanitizing solution, and wherein the pump is in fluid communication with the at least one nozzle.

An embodiment can include a cover for covering the pan, wherein the cover engages with the pan to enclose the second mat from an outside environment. In some embodiments, the pan comprises: four outer sidewalls extending upwardly from the bottom of the pan and forming a pan perimeter; a substantially flat bottom surface of the cavity, wherein the bottom surface is substantially parallel to the bottom of the pan; four inner sidewalls extending upwardly from the bottom surface of the cavity and forming a cavity perimeter of the cavity; and an upper edge positioned between and interconnecting the four inner sidewalls to the four outer sidewalls. An embodiment can include four outer sidewalls that are positioned at an angle greater than about 30 degrees as measured from the bottom of the pan, and wherein the four inner sidewalls are substantially perpendicular to the bottom surface of the cavity. An embodiment can include a cavity perimeter that is substantially concentric with the pan perimeter. An embodiment can include an upper edge that is substantially flat and substantially parallel to the bottom of the pan. An embodiment can include a cover for covering the pan, wherein the cover engages with the upper edge of the pan to enclose the mats from an outside environment. An embodiment can have the second mat and the first mat are sized and shaped to fit in the cavity of the pan. An embodiment can include the first mat is at least about twice as dense as the second mat when the second mat is substantially dry. An embodiment can include a cavity that is formed by a substantially flat bottom surface that is substantially parallel to the bottom of the pan and inner sidewalls extending upwardly from the bottom surface. An embodiment can include at least one liner, film, or coating positioned on at least a bottom surface of the cavity. An embodiment can include a sanitizing solution that is fast-drying and wherein the fast-drying sanitizing solution comprises isopropyl alcohol and quaternary ammoniums. An embodiment can include a pan that is comprised of a substantially non-porous material that inhibits the transmission of moisture, and wherein the absorbent material is comprised of a substantially porous and permeable material that adsorbs the sanitizing solution. An embodiment can include the at least one cutout comprises at least first and second cutouts sized to receive footwear of a user, wherein a weight of the first mat is heavier than a weight of the second mat, wherein the at least one nozzle comprises at least first and second nozzles, each of the first and second nozzles being spatially proximate to a corresponding one of the first and second cutouts, and wherein the fast-drying sanitizing solution is sprayed out of the first nozzle in a substantially flat, longitudinal pattern at least half a length of the first cutout and the sanitizing solution is sprayed out of the second nozzle in a substantially flat, longitudinal pattern at least half a length of the second cutout. An embodiment can include a handrail interconnected to the pan or the floor, wherein the handrail is positioned in a front portion of the system, wherein the cover automatically opens and closes in response to a signal from the controller, and wherein, in a first mode, the controller receives a first signal from the sensor indicating the presence of a user at a first spatial location and opens the cover and, in a second mode, the controller receives a second signal from the sensor indicating the presence of the user at a second spatial location and closes the cover. An embodiment can include a sensor that is one or more of a photoelectric eye, a motion detector, an optical sensor, and a pressure sensor. An embodiment can include at least one cutout that has a rectangular shape, shoe shape, or oval shape.

In one embodiment, a footwear sanitizing system is provided comprising: a pan with a bottom and a cavity that is open to a top opposite the bottom; a plurality of absorbent pads positioned in the cavity of the pan, wherein the absorbent pads are sized and shaped to fit in the cavity of the pan, and wherein the absorbent pads comprise a sanitizing liquid; and a clamping bar interconnected to the pan, wherein the clamping bar is positioned on top of the absorbent pads to hold the absorbent pads in place. An embodiment can also include a cover for covering the pan, wherein the cover engages with the pan to enclose the absorbent pads from an outside environment. An embodiment can include a pan comprising: four outer sidewalls extending upwardly from the bottom of the pan and forming a pan perimeter; a substantially flat bottom surface of the cavity, wherein the bottom surface is substantially parallel to the bottom of the pan; four inner sidewalls extending upwardly from the bottom surface of the cavity and forming a cavity perimeter of the cavity; and an upper edge positioned between and interconnecting the four inner sidewalls to the four outer sidewalls. In some embodiments, the four outer sidewalls can be positioned at an angle greater than about 30 degrees as measured from the bottom of the pan, and wherein the four inner sidewalls are substantially perpendicular to the bottom surface of the cavity. An embodiment can also include a cavity perimeter that is substantially concentric with the pan perimeter. An embodiment can include an upper edge that is substantially flat and substantially parallel to the bottom of the pan. An embodiment can also include a cover for covering the pan, wherein the cover engages with the upper edge of the pan to enclose the absorbent pads from an outside environment. In one embodiment, the clamping bar is interconnected to at least one inner sidewall, wherein the clamping bar is spring-loaded, wherein the clamping bar includes a bar with teeth along one edge, and wherein the teeth engage the upper surface of a top absorbent pad in the plurality of absorbent pads. An embodiment can include a clamping bar that is positioned on a first side of the cavity, wherein the pan further comprises a second clamping bar positioned on a second side of the cavity, and wherein the first side of the cavity is opposite the second side of the cavity. In some embodiments, the cavity is formed by a substantially flat bottom surface that is substantially parallel to the bottom of the pan and inner sidewalls extending upwardly from the bottom surface. An embodiment can also include at least one liner, film, or coating positioned on at least a bottom surface of the cavity. In one embodiment, the sanitizing liquid comprises isopropyl alcohol and quaternary ammoniums. In some embodiments, the pan is comprised of a non-porous material that inhibits the transmission of moisture. An embodiment can also include a handle and a rubber trim around a perimeter of a bottom surface of the cover, wherein the rubber trim engages the pan. An embodiment can also include a sensor, a processor in communication with the sensor, and a motor interconnected to the cover, wherein the sensor senses a user approaching the system and transmits a sensed signal to the processor, wherein the processor controls the motor, and wherein the motor, in response to the sensed signal, moves the cover on and off of the pan.

In some embodiments, a method of sanitizing footwear is provided comprising: providing a pan with a bottom, a cavity that is open to a top opposite the bottom, and a clamping bar; placing a plurality of absorbent pads in the cavity of the pan; releasing the clamping bar; sliding the plurality of absorbent pads under the clamping bar; closing the clamping bar on the plurality of absorbent pads; pouring sanitizing solution onto the plurality of absorbent pads; stepping onto a top absorbent pad; stepping off of the top absorbent pad; and placing a cover on the pan.

In various embodiments, a method of sanitizing footwear is provided comprising providing a pan with a bottom and a cavity that is open to a top opposite the bottom; providing a plurality of absorbent pads positioned in the cavity of the pan, wherein the absorbent pads are sized and shaped to fit in the cavity of the pan, and wherein the absorbent pads comprise a fast-drying sanitizing liquid; providing a cover on the pan and a cover opening mechanism; providing a first sensor for receiving sensor data, including detecting an approaching user; sending the sensor data to a processor, including data regarding the approaching user; sending a signal to the cover opening mechanism instructing the cover opening mechanism to remove the cover from the pan; removing the cover from the pan; sensing the user on the plurality of absorbent pads via a second sensor; sensing the user no longer on the plurality of absorbent pads via the second sensor; and placing the cover back on the pan.

In one embodiment, a footwear sanitizing system is provided comprising: a sanitizer pan; a mat positioned in the sanitizer pan; sanitizing liquid on the mat; and a mat clamping bar interconnected to the sanitizer pan.

In one embodiment, a footwear sanitizing system is provided comprising: a sanitizer pan; an absorbable mat positioned in the sanitizer pan; a heavy mat positioned on top of the absorbable mat within the sanitizer pan, wherein the heavy mat has shoe-shaped cutouts; a pump housing interconnected to the sanitizer pan, the pump housing comprising a photoelectric eye and a nozzle; a pump positioned within the pump housing; a control box interconnected to the pump; and a fluid container interconnected to the pump, wherein the fluid container contains sanitizing solution.

Unless otherwise indicated, all numbers expressing quantities, dimensions, conditions, and so forth used in the specification and claims are to be understood as being modified in all instances by the term "about".

The term "a" or "an" entity, as used herein, refers to one or more of that entity. As such, the terms "a" (or "an"), "one or more," and "at least one" can be used interchangeably herein.

"Absorb" is the incorporation of a substance in one state into another of a different state (e.g. liquids being absorbed by a solid or gases being absorbed by a liquid). Absorption is a physical or chemical phenomenon or a process in which atoms, molecules, or ions enter some bulk phase—gas, liquid or solid material. In most applications, "absorb" means to take in or soak up (energy, or a liquid or other substance) by chemical or physical action, typically gradually.

"At least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C. § 112(f). Accordingly, a claim incorporating the term "means" shall cover all structures, materials, or acts set forth herein, and all of the equivalents thereof. Further, the structures, materials, or acts and the equivalents thereof shall include all those described in the summary of the disclosure, brief description of the drawings, detailed description, abstract, and claims themselves.

Unless otherwise noted, all component or composition levels are in reference to the active portion of that component or composition and are exclusive of impurities, for example, residual solvents or by-products, which may be present in commercially available sources of such components or compositions.

All percentages and ratios are calculated by total composition weight, unless indicated otherwise.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein. By way of example, the phrase from about 2 to about 4 includes the whole number and/or integer ranges from about 2 to about 3, from about 3 to about 4 and each possible range based on real (e.g., irrational and/or rational) numbers, such as from about 2.1 to about 4.9, from about 2.1 to about 3.4, and so on.

These and other advantages will be apparent from the disclosure contained herein. The above-described embodiments, objectives, and configurations are neither complete nor exhaustive. The Summary is neither intended nor should it be construed as being representative of the full extent and scope of the present disclosure. Moreover, references made herein to "the present invention" or "the present disclosure" or aspects thereof should be understood to mean certain embodiments of the present disclosure and should not necessarily be construed as limiting all embodiments to a particular description. The present disclosure is set forth in various levels of detail in the Summary as well as in the attached drawings and the Detailed Description and no limitation as to the scope of the present disclosure is intended by either the inclusion or non-inclusion of elements, components, etc. in this Summary. Additional aspects of the present disclosure will become more readily apparent from the Detailed Description, particularly when taken together with the drawings.

The preceding is a simplified summary of the disclosure to provide an understanding of some aspects of the invention. This summary is neither an extensive nor exhaustive overview of the disclosure and its various embodiments. It is intended neither to identify key or critical elements of the invention nor to delineate the scope of the invention but to present selected concepts of the invention in a simplified form as an introduction to the more detailed description presented below. As will be appreciated, other embodiments of the invention are possible utilizing, alone or in combination, one or more of the features set forth above or described in detail below.

BRIEF DESCRIPTION OF THE DRAWINGS

Those of skill in the art will recognize that the following description is merely illustrative of the principles of the disclosure, which may be applied in various ways to provide many different alternative embodiments. This description is made for illustrating the general principles of the teachings of this disclosure and is not meant to limit the inventive concepts disclosed herein.

The accompanying drawings are incorporated into and form a part of the specification to illustrate several examples of the present invention(s). These drawings, together with the description, explain the principles of the invention(s). The drawings simply illustrate preferred and alternative examples of how the invention(s) can be made and used and are not to be construed as limiting the invention(s) to only the illustrated and described examples. Further features and advantages will become apparent from the following, more detailed, description of the various embodiments of the invention(s), as illustrated by the drawings referenced below.

FIG. 3 is a perspective view of the footwear sanitizing system without a cover.

FIG. 3A is an enlarged view of a portion of FIG. 3.

FIG. 3B is a cross-sectional view of the footwear sanitizing system taken at line B-B of FIG. 3.

FIG. 4A is a perspective view of the footwear sanitizing system with a cover.

FIG. 4B is a side elevation view of the footwear sanitizing system with a cover.

FIG. 5 is a perspective view of the footwear sanitizing system with the cover removed.

Figure 1A:
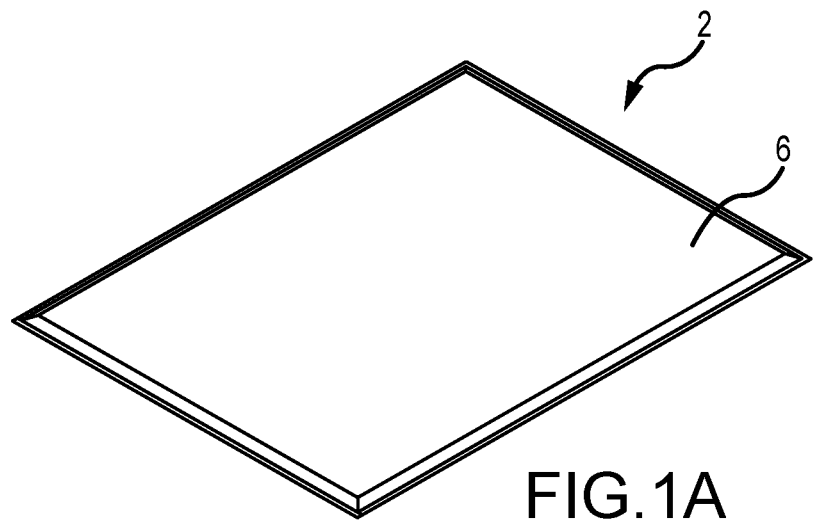
FIG. 1A is a perspective view of a closed package of absorbent pads for the footwear sanitizing system.

To assist in the understanding of the embodiments of the present invention, the following list of components and associated numbering found in the drawings is provided herein:

2 Package of absorbent pads
6 Packaging sleeve
10 Absorbent pad
20 Footwear sanitizing system (without cover)
22 Footwear sanitizing system (with cover)
24 Footwear sanitizing system (with spraying chemical)
26 Pan
30 Outer side (of pan)
34 Bottom (of pan)
38 Cavity (of pan)
40 Bottom surface (of cavity)
42 Inner side (of pan)
50 Clamping bar
54 Bar
58 Teeth or serrated edge (of bar)
62 Tool
70 Front (of system or pan)
74 Rear (of system or pan)
82 Cover
86 Handle
90 Upper edge/surface (of pan)
94 Perimeter edge (of cover)
100 Container of sanitizing solution
104 Sanitizing solution/chemical
108 Shoes
110 Absorbent second mat or middle mat
114 Top mat or first mat
118 Third mat
122 Cutouts or shoe area
126 Pan 130 Outer side (of pan)
134 Bottom (of pan)
138 Cavity (of pan)
142 Inner wall (of cavity)
146 Spray/stream of sanitizing solution
150 Handrail
154 Pump housing
158 Sensor
162 Nozzle
166 Sanitizing solution container
170 Fluid line
174 Control box
178 Power chord
182 Control line
190 Automatic handwashing station
192 Openings for hands It should be understood that the drawings are not necessarily to scale, and various dimensions may be altered. In certain instances, details that are not necessary for an understanding of the invention or that render other details difficult to perceive may have been omitted. It should be understood, of course, that the invention is not necessarily limited to the particular embodiments illustrated herein.

DETAILED DESCRIPTION

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

Figure 1B:
FIG. 1B is a side elevation view of the closed package of absorbent pads for the footwear sanitizing system.

FIG. 1A is a perspective view of a closed package 2 of absorbent pads for the footwear sanitizing system. FIG. 1B is a side elevation view of the closed package 2 of absorbent pads for the footwear sanitizing system. The package 2 includes a sealed packaging sleeve 6. The sealed packaging sleeve 6 encloses the absorbent pads. As mentioned above, the absorbent pads may be dry or pre-saturated. If the pads are pre-saturated, then the material of the packaging sleeve 6 must not permit the transmission of the sanitizing chemical such that the pads do not dry out and the edges of the packaging sleeve 6 must be sealed to prevent the pads from drying out.

Figure 2A:
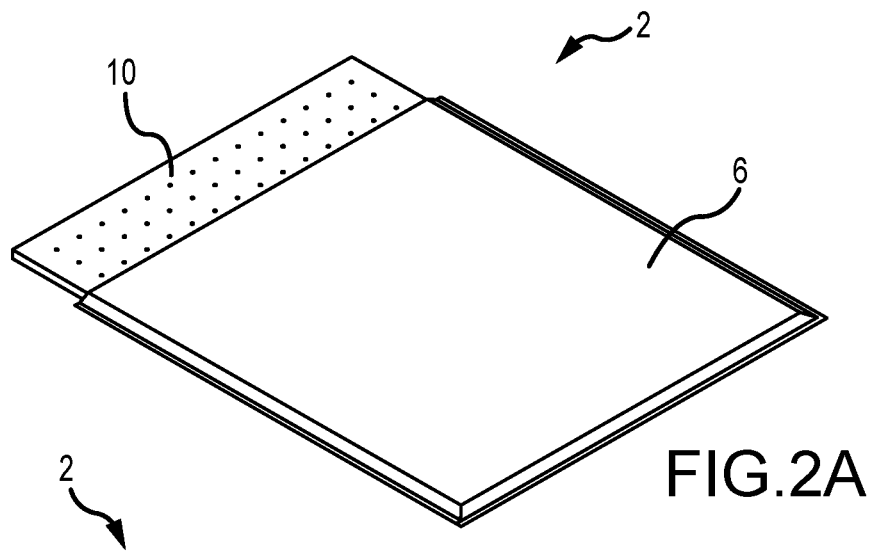
FIG. 2A is a perspective view of an open package of absorbent pads for the footwear sanitizing system.
Figure 2B:
FIG. 2B is a side elevation view of the open package of absorbent pads for the footwear sanitizing system.

FIG. 2A is a perspective view of an open package 2 of absorbent pads 10 for the footwear sanitizing system. FIG. 2B is a side elevation view of the open package 2 of absorbent pads 10 for the footwear sanitizing system. The sleeve 6 contains one absorbent pad 10. In other embodiments, the packaging sleeve 6 contains two or more absorbent pads 10.

In the embodiment shown, the pads 10 are rectangular shaped. However, in other embodiments the pads may have different shapes such as round, oval, circular, square, or any other shape. In some embodiments, the pads are between about 6 inches and about 24 inches wide. In a typical embodiment, the pads are between about 12 inches and about 20 inches wide. More typically, the pads are about 17.75 inches wide. In some embodiments, the pads are between about 10 inches and about 28 inches long (measured from front to rear or toe to heel). In a typical embodiment, the pads are between about 14 inches and about 22 inches long. More typically, the pads are about 20.75 inches long.

The pads can vary in thickness depending on the specific use, size, and sanitizing chemical used. For example, the pads may be between about 0.05 inch and about 1.0 inch thick. Typically, the pads are between about 0.0625 inch and about 0.5 inch thick. More typically, the pads are about 0.125 inch thick.

In some embodiments, the pads 10 are pre-saturated with the sanitizing solution and can be used immediately after being placed in the pan or tray. In other embodiments, the pads 10 are substantially dry and the user adds the sanitizing solution to the pads 10 once they are placed in the pan. Because the pads must hold the sanitizing solution and deposit the solution onto the soles of a user's shoes when the user steps on the pad, the pads must be absorbent. The pad may be sponge-like to permit the sanitizing liquid to move through the pad when the user steps on the pad. The pads may contain a negative charge to help attract "dipolar" water or other molecules in the sanitizing solution and absorb them. Additionally, or alternatively, the pads may be comprised of fibers that have papillary action, meaning the fibers draw or suck in the liquid sanitizer like a straw through the interior of the fiber. The liquid is then stored in the interior cell walls until it eventually dries out or evaporates.

Desired characteristics of the pad include the desired absorbency, texture, abrasive upper surface, density, weight, backing, and thickness. For example, the typical absorbency of the pad is 164 mL/ft$^2$. A more typical absorbency of the pad is 410 mL per pad. The permeability and/or porosity of the pad can also be important as the pores/channels can also absorb and/or transport the liquid sanitizer. Thus, the number of pores/capillaries/channels per square inch and the size thereof also affects the absorption rate and qualities of the pad.

The typical texture of the pad is rough, mildly abrasive, & soft. A more typical texture of the pad is mildly abrasive. In some embodiments, it may be desirable for the upper surface of the pad (the surface that touches the sole of the user's shoes) to have an abrasive texture such that the user does not slip on the pad, to remove debris from the user's footwear, and to increase the amount and rate the sanitizer transfers to the user's shoes' soles. Alternatively, a smooth upper surface may be desired such that the user's shoes do not stick to and rip the absorbent pad. The typical abrasiveness of the upper surface of the pad is mildly abrasive.

The typical density of the pad is between light weight and medium weight, for example between about 5.0 lb/ft$^3$ and about 15.0 lb/ft$^3$ (about 80 kg/m$^3$ and about 240 kg/m$^3$). A more typical density of the pad is a medium weight density, for example about 11.0 lb/ft$^3$ (about 176 kg/m$^3$). The weight of the pad and material used therein can affect the amount of sanitizer solution that can be absorbed and how quickly the liquid solution spreads (wicking time (seconds) or level (measured in cm or inches)) throughout the pad. The typical weight of the pad is between about 0.1 lb and about 1.5 lb. A more typical weight of the pad is about 0.29 lb.

The absorbent pads may be comprised of multiple materials and layers. In some embodiments, the pads are comprised of felt material. In other embodiments, the pad can be comprised of cotton, polyester, cellulose, and polypropylene materials. The pads may comprise cellulose to make the pad absorbent. The pads may be comprised of natural and/or synthetic materials. Further, the pad may include gels, crystals, or beads that absorb moisture, such as Super Absorbent Polymer (SAP) or Absorbent Gel Material (AGM). Superabsorbent polymers are commonly made from the polymerization of acrylic acid blended with sodium hydroxide in the presence of an initiator to form a polyacrylic acid sodium salt (sometimes referred to as sodium polyacrylate). This polymer is the most common type of SAP made in the world today. Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile to name a few. The latter is one of the oldest SAP forms created. Today superabsorbent polymers are made using one of three primary methods: gel polymerization, suspension polymerization, or solution polymerization.

The pads 10 may have multiple layers for various purposes. For example, the bottom layer of the pad 10 may be a non-absorbent material (e.g., plastic, other polymer, cellophane, cellulose, etc.) to keep the sanitizing solution in the pad 10 when the system includes a stack of pads 10. Here, the sanitizing solution will stay in the upper pads in the stack of pads 10 rather than seeping into and staying in the bottom pad in the stack. The middle layer of the pad 10 may be an absorbent material for absorbing and holding the sanitizing solution. The upper layer of the pad 10 may be a stronger material that withstands repeatedly being stepped on by the users of the system. Thus, the upper layer is less likely to tear after a user steps onto and off of the pad. Because the upper layer is stronger, it will likely be less absorbent than the middle layer and, therefore, may have perforations to permit the sanitizing solution to move from the middle layer to the soles of the user's shoes. The upper layer may also be smooth to reduce the amount it sticks to the user's shoes and, thus, minimize tearing. Alternatively, the upper layer may have an abrasive surface to permit more sanitizing solution to adhere to the user's shoes.

FIG. 3 is a perspective view of the footwear sanitizing system 20 without a cover. FIG. 3A is an enlarged view of a portion of FIG. 3. FIG. 3B is a cross-sectional view of the footwear sanitizing system 20 taken at line B-B of FIG. 3. The footwear sanitizing system 20 includes a pan 26 to hold the absorbent pads 10, and a clamping bar 50.

The pan 26 is rectangular shaped and includes four outer sides 30, a bottom 34, and a cavity 38 formed by multiple inner sides (also called "inner sidewalls" herein) 42 and a bottom surface 40. The bottom 34 may have an abrasive surface, rubber, or other coating or layer to prevent slipping on a flat, smooth floor. Alternatively, the pan 26 may be bolted to the floor or secured to the floor in another known manner. The four outer sides 30 extend upwardly from the bottom 34. The inner sides 42 extend upwardly from the bottom surface 40 of the cavity. The bottom 34 is positioned on the floor; thus, the bottom 34 is substantially flat. For example, in one embodiment, the outer sides 30 of the pan 26 are positioned at an angle between about 30° and about 75° as measured from the bottom 34 of the pan 26. In a typical embodiment, the outer sides 30 of the pan 26 are positioned at an angle between about 40° and about 60° as measured from the bottom 34 of the pan 26. The outer sides 30 may be sloped (as shown) or vertical and substantially perpendicular to one another. The outer sides 30 terminate in a substantially flat (horizontal or angled inward) edge 90. The upper edge 90 is positioned between and connects the outer sides 30 and the inner sides 42. The pan 26 has a cavity 38 for holding the pads 10. The inner sides 42 and bottom surface 40 form the cavity 38 and the inner sides 42 may be substantially vertical (as shown) or may slope inward or outward. Here, the inner sides 42 are substantially straight to align with the substantially straight sides of the pads 10. Alternatively, the inner sides 42 may be curved or another shape to match the shape of the pads 10. The cavity 38 may be approximately the same shape and size of the pads 10 for securely holding the pads 10. The bottom surface 40 of the cavity 38 is substantially flat and substantially parallel to the bottom 34 of the pan 26.

The pan 26 may be composed of a metal material, plastic material, composite material, acrylic material, ceramic material, glass, glass-like material, or other sturdy material that does not absorb moisture and prevents the transmission or evaporation of liquid and that does not react with the sanitizing chemical. Thus, any material can be used, but preferred characteristics of the pan material include strength (the material should be strong and not break or fracture if kicked or stepped on), little to no absorption of liquid (the liquid in the pads should stay in the pads and not be soaked up by the pan), limit the transmission of the liquid out of the pan (to prevent and limit evaporation of the sanitizing chemical), and not degrade due to constant contact with the sanitizing chemical.

The pan 26 may also have a liner, film, or coating along the cavity 38 (including the bottom 40 of the cavity and the inner sidewalls 42) to protect the pan 26 from the chemicals used in the sanitizing solution, i.e., to prevent the pan 26 from degrading or reacting with the chemicals used in the sanitizing solution.

In one embodiment, the system 20 includes a first clamping bar 50 positioned at the front 70 of the pan 26 and a second clamping bar 50 at the rear 74 of the pan 26. The clamping bar 50 may be a spring-loaded bar 54. The user uses a tool 62 (e.g., screw driver) to push on an end of the bar 54 to express the spring of the clamping bar 50 and lift the bar 54. In other embodiments, the clamping bar 50 may not have a spring and rather may be raised and lowered by screwing or unscrewing a screw in one or both ends of the bar 54 or the center of the bar 54. In still other embodiments, the clamping bar 50 may not have a spring or screw to raise and lower the bar 54. Rather, the bar may be heavy and keep the pads 10 in place using its weight and a serrated edge 58.

The bar 54 may have a serrated edge or an edge with teeth 58 that interacts with and is positioned adjacent to the pad 10. The serrations or teeth 58 assist the bar 54 in gripping and holding the pads 10. Other embodiments may have more or fewer clamping bars 50 or other securing mechanisms. The purpose of the clamping bar 50 is to hold the pad 10 in place as the user steps onto and off of the pad 10. When the upper pad needs to be removed or new pads 10 put into the pan 26, then the user opens or loosens the clamping bar 50 or other securing mechanism to permit the removal and replacement of the pads 10.

As shown in FIG. 3B, the pan 26 can hold one or more pads 10. For example, two or more pads 10 may be placed in the pan 26. The user steps onto the top pad 10. As the top pad 10 wears out, gets dirty, or dries out, the user (or operator) can remove the top pad 10. Then the system continues to function as the users now step on the second pad, which is now the top pad 10, to sanitize the soles of their shoes. As discussed above, if six pads 10 are needed per day, then the six pads 10 may be placed in the pan 26 at the beginning of the day. As the day progresses, the operator removes the top pad 10. By the end of the day, all of the pads 10 should be gone and the operator will refill the pan 26 with a new pack of six pads.

FIG. 4A is a perspective view of the footwear sanitizing system 22 with a cover 82. FIG. 4B is a side elevation view of the footwear sanitizing system 22 with a cover 82. FIG. 5 is a perspective view of the footwear sanitizing system 22 with the cover 82 removed. The cover 82 can be placed on the pan 26 after each use, nightly, or between shifts depending on the frequency of use of the system 22. The cover 82 may be optional and provided for the pan 26 for longer gaps between uses in order to prevent the pads 10 from drying out. Because a quick-drying sanitizing chemical is used, the pads 10 will dry out quicker than with slow-drying sanitizing agents. Thus, the cover 82 slows the drying-out process. The cover 82 is likely the same material as the pan 26, but the cover 82 can be a different material in some embodiments. The cover should reduce the amount of liquid sanitizer evaporating from the pan 26 and pads 10. Thus, the cover 82 should be comprised of a non-porous material that inhibits the transmission of moisture or blocks moisture from evaporating from the pads and into the environment. Further, the cover 82 is likely comprised of a non-absorbent material, like the pan 26.

The cover 82 may be flat (i.e., have a substantially flat upper surface and substantially flat lower surface with a perimeter edge 94) and have a handle 82. The user can remove the cover 82 using the handle 86. The cover 82 is sized and shaped to fit on or in the pan 26. In the embodiment shown, the cover 86 sits on a portion of the upper edge 90 of the pan 26. The cover 82 may be sized such that it sits on and covers the entire upper edge 90. Alternatively, the cover 82 may be slightly smaller than the outer perimeter of the upper edge 90 and, therefore, sit on only a portion of the upper edge 90. In some embodiments, the cover 82 (outer perimeter of the cover) is smaller than the inner perimeter of the upper edge 90 such that the cover 82 sits in the pan 26 within the upper edge 90. The cover 82 may sit directly on the pads 10 or sit on the clamping bar 50. In some embodiments, the upper edge 90 is angled slightly inward and the cover 82 sits on a lower/inner portion of the upper edge 90. In other embodiments, the cover 82 may be larger (have a larger outer perimeter) than the upper edge 90. Thus, a portion of the cover 82 would protrude over the outer perimeter of the upper edge 90. In some embodiments, the cover 82 has downward-oriented sidewalls positioned around the perimeter edge 94 of the cover 82. The downward-oriented sidewalls may be substantially perpendicular to the upper surface of the cover 82 or the downward-oriented sidewalls may be angled to correspond to the angle of the outer sides 30. The cover 82 may have a rubber trim around the perimeter edge 94, around the perimeter of the bottom surface of the cover 82, or along the underside of the angled sidewalls to assist the cover 82 in securely engaging the pan 26 and to limit the amount of moisture that can evaporate from the pads 10.

In some embodiments, the under or bottom surface of the cover 82 may have a liner, film, or coating (similar to one embodiment of the pan 26) to protect the cover 82 from the chemicals used in the sanitizing solution, i.e., to prevent the cover from degrading or reacting with the chemicals used in the sanitizing solution.

In some embodiments (not shown), the cover is two or more pieces that slide apart and slide together to cover the pan. For example, the cover may be two pieces of the same or different sizes that slide together to cover the pan. Thus, the cover or cover pieces may be positioned on a track to assist in sliding on and off the pan. If the cover is two pieces, then the two pieces will meet at a seam. The pieces may interconnect with one another at the seam through the use of rubber trim, a tongue and groove connection, a friction fit, snaps, one piece overlapping the other piece a predetermined distance, or any other known interconnection means. In some embodiments, the edge of at least one piece at the seam has a rubber trim to assist in engaging the edge of the second piece and to limit the gap through which moisture can escape from the pan.

The cover 82 may be operated manually by the user, i.e., by lifting the cover 82 using the handle 86. The cover 82 may be manually slid along tracks by the user, which is possible if the cover 82 is one piece (as shown) or two or more pieces. Alternatively, the cover 82 may be automatically operated. For example, the system can include sensors to sense a user approaching and then a motor moves the cover 82 off of the pan 26. The motor may slide the cover (or cover pieces if the cover is comprised of two or more pieces) along tracks and off of the pan 26. The cover or cover pieces may be moved to open and close the system 22 using a track and pulley system. An embodiment of the system 22 with the automatic cover 82 may also include a button the user can press to retract or move the cover 82 in case the sensor(s) does not function properly and the cover 82 does not open when the user approaches the footwear sanitizing system 22.

Examples of the various sensors may include, but are in no way limited to, motion sensors, weight or pressure sensors, audio sensors, photoelectric sensors, broken beam sensors, thermal sensors, a ranging and imaging system (e.g., LIDAR, etc.), LIDAR (Light Imaging, Detection, And Ranging) systems, an imaging sensor (e.g., camera, IR, etc.), cameras (e.g., independent, stereo, combined image, etc.), infrared (IR) sensors, a radio object-detection and ranging system sensors (e.g., RADAR, RF, etc.), RADAR sensors (e.g., object-detection sensors and/or systems), radio frequency (RF) sensors, ultrasonic sensors (e.g., transducers, transceivers, etc.), and other ranging, imaging, and/or object-detecting sensors. In some embodiments, the sensors and systems may be disposed in and around one or more portions of a footwear sanitizing system 22 (e.g., the surrounding floor, vertically in front of the system, attached to a handwashing station, above the system 22, on a ceiling, on a wall, on or in a sidewall 30 of the pan 26, on an upper surface of the cover 82, etc.). In some embodiments, the sensors may be used to monitor and/or detect a position of persons near, or proximal to, the system 22.

The sensor(s) used to detect an approaching user may be a photoelectric sensor, or photo eye, which is an equipment used to discover the distance, absence, or presence of an object by using a light transmitter, often infrared, and a photoelectric receiver. There are three different useful types: opposed (through beam), retro-reflective, and proximity-sensing (diffused). A self-contained photoelectric sensor contains the optics, along with the electronics. It requires only a power source.

Remote photoelectric sensors used for remote sensing contain only the optical components of a sensor. The circuitry for power input, amplification, and output switching are located elsewhere, typically in a control panel. This allows the sensor, itself, to be very small. Also, the controls for the sensor are more accessible, since they may be bigger.

The sensor may have a through beam arrangement, which consists of a receiver located within the line-of-sight of the transmitter. In this mode, an object is detected when the light beam is blocked from getting to the receiver from the transmitter. A retroreflective arrangement places the transmitter and receiver at the same location and uses a reflector to bounce the inverted light beam back from the transmitter to the receiver. An object is sensed when the beam is interrupted and fails to reach the receiver. Alternatively, the system may use a proximity-sensing (diffused) arrangement where the transmitted radiation must reflect off the object in order to reach the receiver. In this mode, an object is detected when the receiver sees the transmitted source rather than when it fails to see it. As in retro-reflective sensors, diffuse sensor emitters and receivers are located in the same housing. But the target acts as the reflector, so that detection of light is reflected off the disturbance object. The emitter sends out a beam of light (most often a pulsed infrared, visible red, or laser) that diffuses in all directions, filling a detection area. The target then enters the area and deflects part of the beam back to the receiver. Detection occurs and output is turned on or off when sufficient light falls on the receiver. Some photo eyes have two different operational types, light operate and dark operate. Light operate photo eyes become operational when the receiver "receives" the transmitter signal. Dark operate photo eyes become operational when the receiver "does not receive" the transmitter signal. The detecting range of a photoelectric sensor is its "field of view," or the maximum distance from which the sensor can retrieve information, minus the minimum distance. A minimum detectable object is the smallest object the sensor can detect.

The system 22 may also include infrared (IR) break-beam sensors, which are a simple way to detect motion. They work by having an emitter side that sends out a beam of IR light and a receiver side with a receiver across the way that is sensitive to the IR light. If that ray has been interrupted, the cover will be removed from the system 22 and the system 22 will open for use.

The infrared (IR) sensors may include one or more components configured to detect image information associated with an environment of the system 22. The IR sensors may be configured to detect targets in low-light, dark, or poorly-lit environments. The IR sensors may include an IR light emitting element (e.g., IR light emitting diode (LED), etc.) and an IR photodiode. In some embodiments, the IR photodiode may be configured to detect returned IR light at or about the same wavelength to that emitted by the IR light emitting element. In some embodiments, the IR sensors may include at least one processor configured to interpret the returned IR light and determine locational properties of targets. The IR sensors may be configured to detect and/or measure a temperature associated with a person or object approaching the system 22. Examples of IR sensors as described herein may include, but are not limited to, at least one of Opto Diode lead-salt IR array sensors, Opto Diode OD-850 Near-IR LED sensors, Opto Diode SA/SHA727 steady state IR emitters and IR detectors, FLIR® LS microbolometer sensors, FLIR® TacFLIR 380-HD InSb MWIR FPA and HD MWIR thermal sensors, FLIR® VOx 640×480 pixel detector sensors, Delphi IR sensors, other industry-equivalent IR sensors and/or systems, and may perform IR visual target and/or obstacle detection in an environment around the system 22 using any known or future-developed standard and/or architecture.

The LIDAR sensor may include one or more components configured to measure distances to targets using laser illumination. In some embodiments, the LIDAR sensor may provide 3D imaging data of an environment around the system 22. The imaging data may be processed to generate a full 360-degree view of the environment around the system 22. The LIDAR sensor may include a laser light generator configured to generate a plurality of target illumination laser beams (e.g., laser light channels). In some embodiments, this plurality of laser beams may be aimed at, or directed to, a rotating reflective surface (e.g., a mirror) and guided outwardly from the LIDAR sensor into a measurement environment. The rotating reflective surface may be configured to continually rotate 360 degrees about an axis, such that the plurality of laser beams is directed in a full 360-degree range around the system 22. A photodiode receiver of the LIDAR sensor may detect when light from the plurality of laser beams emitted into the measurement environment returns (e.g., reflected echo) to the LIDAR sensor. The LIDAR sensor may calculate, based on a time associated with the emission of light to the detected return of light, a distance from the system 22 to the illuminated target. In some embodiments, the LIDAR sensor may generate over 1.0 million points per second and have an effective operational range of at least 10 meters. Examples of the LIDAR sensor as described herein may include, but are not limited to, at least one of Velodyne® LiDAR™ HDL-64E 64-channel LIDAR sensors, Velodyne® LiDAR™ HDL-32E 32-channel LIDAR sensors, Velodyne® LiDAR™ PUCK™ VLP-16 16-channel LIDAR sensors, Leica Geosystems Pegasus:Two mobile sensor platform, Garmin® LIDAR-Lite v3 measurement sensor, Quanergy M8 LiDAR sensors, Quanergy S3 solid state LiDAR sensor, LeddarTech® LeddarVU compact solid state fixed-beam LIDAR sensors, other industry-equivalent LIDAR sensors and/or systems, and may perform illuminated target and/or obstacle detection in an environment around the system 22 using any known or future-developed standard and/or architecture.

The RADAR sensors may include one or more radio components that are configured to detect persons in an environment of the system 22. In some embodiments, the RADAR sensors may determine a distance, position, and/or movement vector (e.g., angle, speed, etc.) associated with the person over time. The RADAR sensors may include a transmitter configured to generate and emit electromagnetic waves (e.g., radio, microwaves, etc.) and a receiver configured to detect returned electromagnetic waves. In some embodiments, the RADAR sensors may include at least one processor configured to interpret the returned electromagnetic waves and determine locational properties of targets. Examples of the RADAR sensors as described herein may include, but are not limited to, at least one of Infineon RASIC™ RTN7735PL transmitter and RRN7745PL/46PL receiver sensors, Autoliv ASP Vehicle RADAR sensors, Delphi L2C0051TR 77 GHz ESR Electronically Scanning Radar sensors, Fujitsu Ten Ltd. Automotive Compact 77 GHz 3D Electronic Scan Millimeter Wave Radar sensors, other industry-equivalent RADAR sensors and/or systems, and may perform radio target and/or obstacle detection in an environment around the system 22 using any known or future-developed standard and/or architecture.

The ultrasonic sensors may include one or more components that are configured to detect objects/targets in an environment of the system 22. In some embodiments, the ultrasonic sensors may determine a distance, position, and/or movement vector (e.g., angle, speed, etc.) associated with a target over time. The ultrasonic sensors may include an ultrasonic transmitter and receiver, or transceiver, configured to generate and emit ultrasound waves and interpret returned echoes of those waves. In some embodiments, the ultrasonic sensors may include at least one processor configured to interpret the returned ultrasonic waves and determine locational properties of targets. Examples of the ultrasonic sensors as described herein may include, but are not limited to, at least one of Texas Instruments TIDA-00151 automotive ultrasonic sensor interface IC sensors, Max-Botix® MB8450 ultrasonic proximity sensor, MaxBotix® ParkSonar™-EZ ultrasonic proximity sensors, Murata Electronics MA40H1S-R open-structure ultrasonic sensors, Murata Electronics MA40S4R/S open-structure ultrasonic sensors, Murata Electronics MA58MF14-7N waterproof ultrasonic sensors, other industry-equivalent ultrasonic sensors and/or systems, and may perform ultrasonic target and/or obstacle detection in an environment around the system 22 using any known or future-developed standard and/or architecture.

The motion sensors may detect motion and/or movement of persons approaching or near the system 22. Optionally, the motion sensors may be used alone or in combination to detect movement. For example, a user may walk near the system 22 but not approach the system 22 because he/she does not intend to use the system 22 to sanitize his/her shoes. The sensors should be calibrated or programmed to tell the difference between intended users of the system and passersby and respond accordingly.

Weight sensors may be employed to collect data relating to users approaching the system 22. In some cases, the weight sensors may be included in the floor proximate a system 22. Alternatively, the system 22 may also include a mat near the system and the mat has one or more weight sensors embedded therein. The mat may be interconnected to the pan and positioned at the rear of the pan such that the user steps on the mat before stepping on the pad in the system 22. The system 22 may also have weight sensors under the pan 26 or in the pan 26 under the pads 10 such that the system 22 knows when the user is no longer standing on the pad 10 in the pan 26.

The system 22 may include audio sensors configured to receive audio input from a user of the system 22. The audio input from a user may correspond to voice commands. For example, as the user approaches the footwear sanitizing system 22, the user can say, "Open," which causes the system 22 to move the cover 82 off of the pan 26. Audio sensors 321 may include, but are not limited to, microphones and other types of acoustic-to-electric transducers or sensors. Optionally, the audio sensors may be configured to receive and convert sound waves into an equivalent analog or digital signal. The audio sensors may determine one or more locations associated with various sounds from a user. The location of the sounds may be determined based on a comparison of volume levels, intensity, and the like. For example, the system 22 may be configured only respond to voice commands that are of a certain volume or determined to be a certain distance from the system 22 such that the system does not respond to conversations by people a certain distance away from the system 22, who likely are not immediately intending to use the footwear sanitizing system. As can be appreciated, the number of sound receivers used in the system 22 may be increased (e.g., two or more than two) to increase measurement accuracy surrounding sound detection and location, or source, of the sound (e.g., via triangulation, etc.).

In some embodiments, the system 22 may include other sensors and/or combinations of the sensors described above. Additionally or alternatively, one or more of the sensors described above may include one or more processors configured to process and/or interpret signals detected by the one or more sensors. In some embodiments, the processing of at least some sensor information provided by the sensors may be processed by at least one sensor processor. Raw and/or processed sensor data may be stored in a sensor data memory storage medium. In some embodiments, the sensor data memory may store instructions used by the sensor processor for processing sensor information provided by the sensors and systems. In any event, the sensor data memory may be a disk drive, optical storage device, solid-state storage device such as a random access memory ("RAM") and/or a read-only memory ("ROM"), which can be programmable, flash-updateable, and/or the like.

Each sensor may include an operational detection range and operational detection angle. The operational detection range may define the effective detection limit, or distance, of the sensor. In some cases, this effective detection limit may be defined as a distance from a portion of the sensor (e.g., a lens, sensing surface, etc.) to a point in space offset from the sensor. The effective detection limit may define a distance, beyond which, the sensing capabilities of the sensor deteriorate, fail to work, or are unreliable. In some embodiments, the effective detection limit may define a distance, within which, the sensing capabilities of the sensor are able to provide accurate and/or reliable detection information. The operational detection angle may define at least one angle of a span, or between horizontal and/or vertical limits, of a sensor. As can be appreciated, the operational detection limit and the operational detection angle of a sensor together may define the effective detection zone (e.g., the effective detection area, and/or volume, etc.) of a sensor.

Sensor data and information (also referred to as a "sensor signal" herein) may be collected by one or more sensors. This information may be processed (e.g., via a processor, computer-vision system, etc.) to determine targets (e.g., people) inside one or more detection zones associated with the system 22.

The system 22 with an automatic cover may also include communication system with one or more sensors, sensor processors, sensor data memory, cover control system, communications subsystem, control data, computing devices, display devices, and other components that may be associated with the system 22. These associated components may be electrically and/or communicatively coupled to one another via at least one bus. In some embodiments, the one or more associated components may send and/or receive signals across a communication network to a control source or some other entity.

The cover control system may receive processed sensor information from the sensor processor and determine to control an aspect of the system 22, e.g., the cover. Controlling an aspect of the system 22 may include sending commands to one or more computing devices associated with the system 22. In this example, the control system may receive sensor data describing an environment surrounding the system 22 and, based on the sensor data received, determine to adjust the cover 82, lighting surrounding the system 22, and sanitizing solution amount present in the pad 10.

Figure 6:
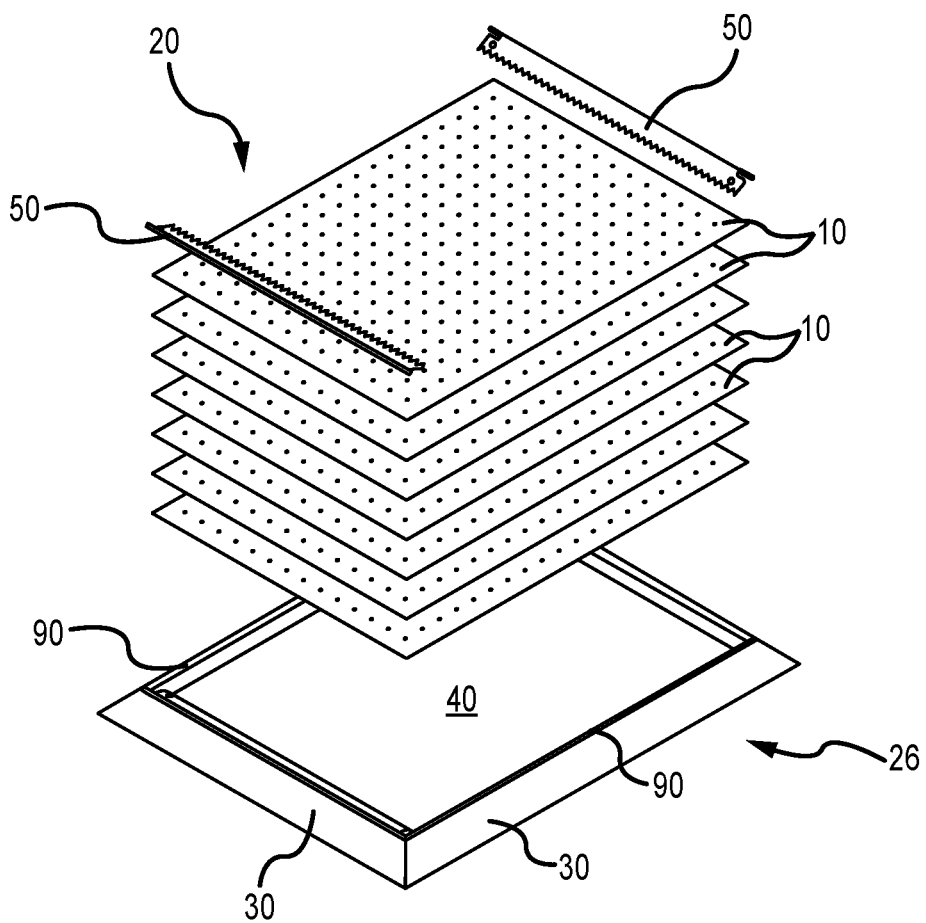
FIG. 6 is an exploded view of the footwear sanitizing system without a cover.

FIG. 6 is an exploded view of the footwear sanitizing system 20 without a cover. The system 20 is shown with seven pads 10, two clamping bars 50, and a pan 26. In the embodiment shown, the pan 26 includes four outer sidewalls 30 extending upwardly from the bottom of the pan 26 and forming a pan perimeter. The pan 26 has a substantially flat bottom surface 40 of the cavity 38, where the bottom surface 40 is substantially parallel to the bottom of the pan 26. Four inner sidewalls 42 extend upwardly from the bottom surface 40 of the cavity 38 and form a cavity perimeter of the cavity 38. The pan 26 has an upper edge 90 positioned between and interconnecting the four inner sidewalls 42 to the four outer sidewalls 30 and the cavity perimeter is substantially concentric with the pan perimeter.

Figure 7:
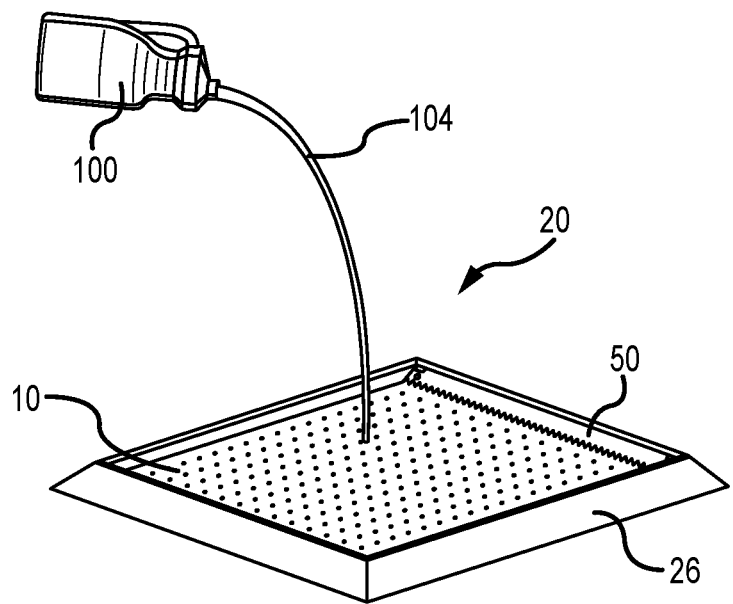
FIG. 7 is a perspective view of the footwear sanitizing system with dry pads and sanitizing solution being added to the pads.

FIG. 7 is a perspective view of the footwear sanitizing system 20 with dry pads 10 and sanitizing solution 104 being added to the pads 10. The sanitizing solution 104 is poured onto the pads 10 from a container 100. In one embodiment, the sanitizing solution 104 is ready to use and does not need to be diluted with water. In other embodiments, the sanitizing solution 104 is concentrated and must be diluted with water or alcohol.

Figure 8:
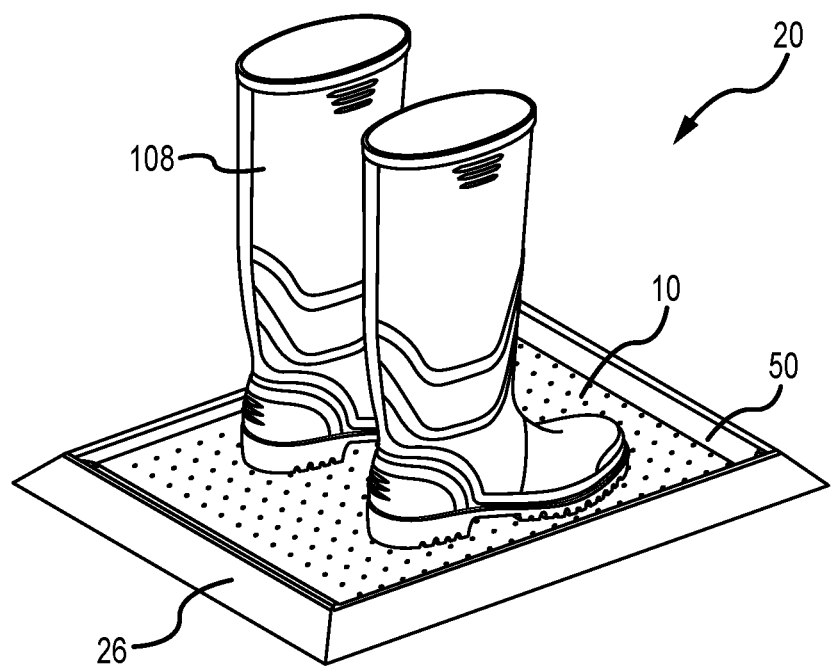
FIG. 8 is a perspective view of the footwear sanitizing system with shoes positioned on the pad of the system.

FIG. 8 is a perspective view of the footwear sanitizing system 20 with shoes 108 positioned on the pad 10 of the system 20. The user steps into the pan 26 and onto the pad 10 such that the bottom (soles) of the user's shoes 108 are positioned on the upper surface of the pad 10. The sanitizing solution is transferred from the pad 10 to the soles of the user's shoes 108.

Figure 9:
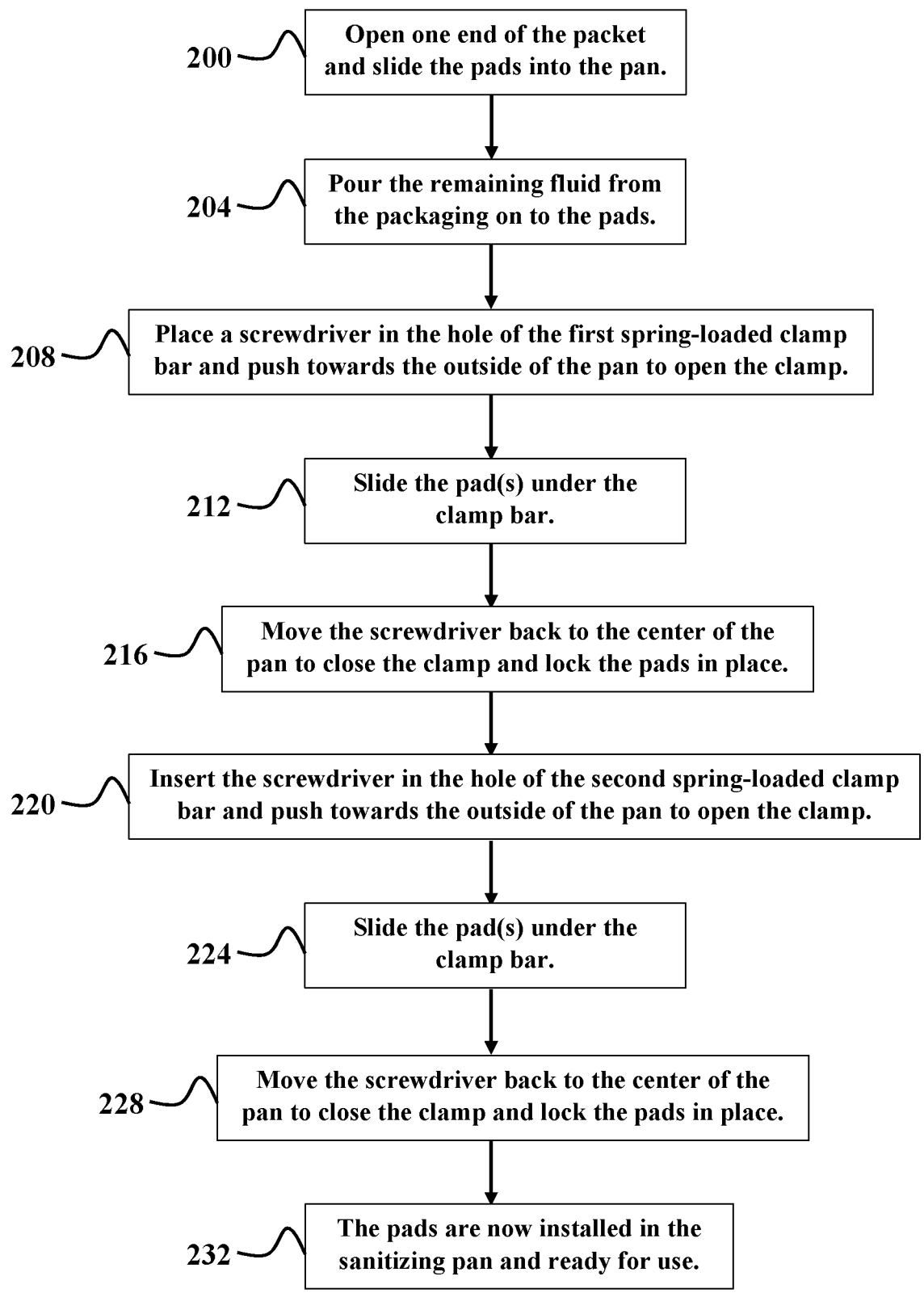
FIG. 9 is a flowchart showing the installation process for installing the pre-saturated pads into the pan.

FIG. 9 is a flowchart showing the installation process for installing the pre-saturated pads into the pan. With the packet of pads in the sanitizing pan, open one end of the packet and slide the pads into the pan 200. Pour the remaining fluid from the packaging on to the pads 204. Place a screwdriver in the hole of the first spring-loaded clamping bar and push towards the outside of the pan to open the clamp 208. Slide the pad or pads under the clamping bar 212 and move the screwdriver back to the center of the pan to close the clamp and lock the pads in place 216. Insert the screwdriver in the hole of the second spring-loaded clamping bar and push towards the outside of the pan to open the clamp 220. Slide the pad or pads under the clamping bar 224 and move the screwdriver back to the center of the pan to close the clamp and lock the pads in place 228. The pads are now installed in the sanitizing pan and ready for use 232.

Figure 10:
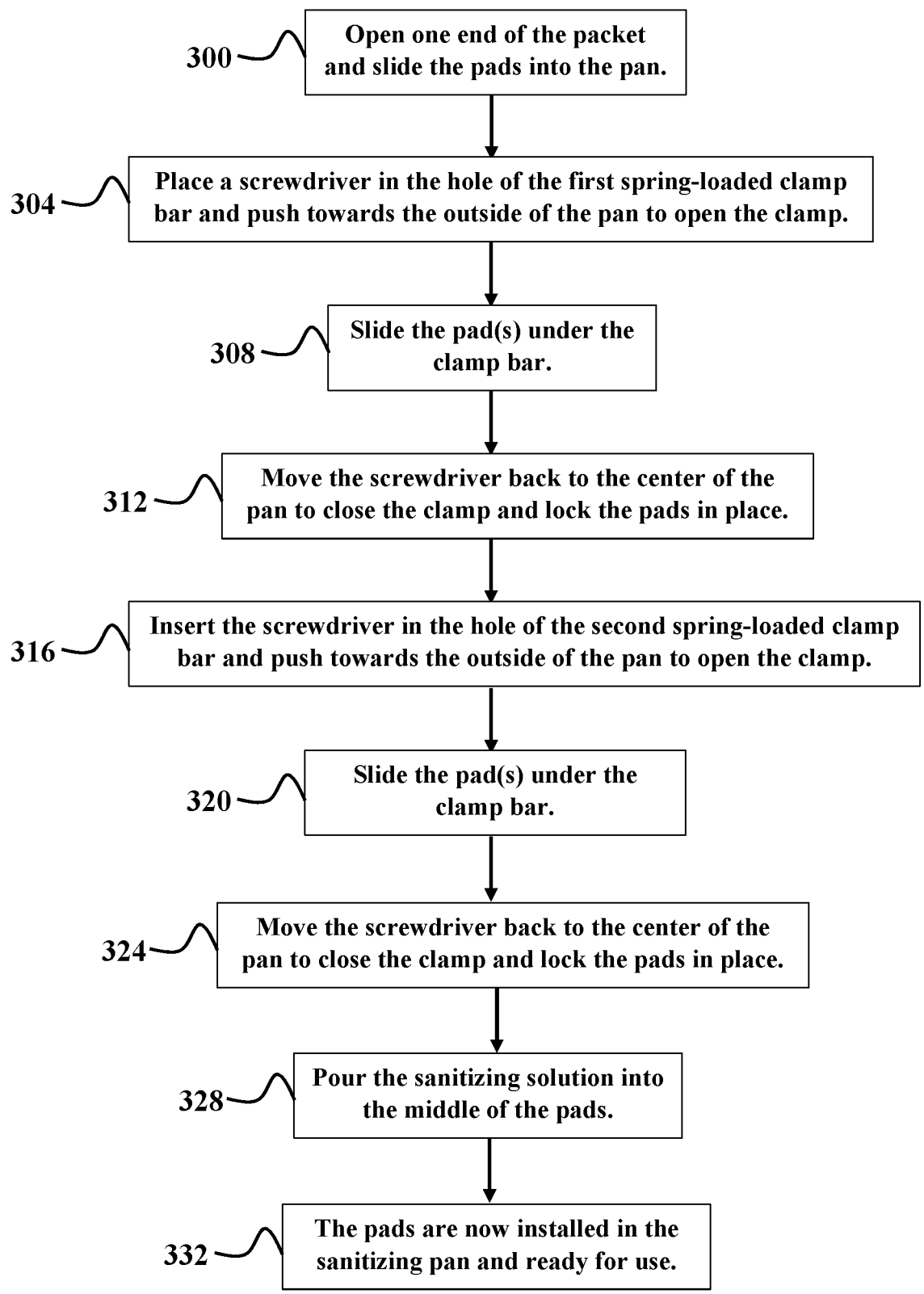
FIG. 10 is a flowchart showing the installation process for installing the dry pads into the pan.

FIG. 10 is a flowchart showing the installation process for installing the dry pads into the pan. With the packet of pads in the sanitizing pan, open one end of the packet and slide the pads into the pan 300. Place a screwdriver in the hole of the first spring-loaded clamping bar and push towards the outside of the pan to open the clamp 304. Slide the pad or pads under the clamping bar 308 and move the screwdriver back to the center of the pan to close the clamp and lock the pads in place 312. Insert the screwdriver in the clamping bar hole of the second spring-loaded clamping bar (which may be on the opposite end of the pan) and push towards the outside of the pan to open the clamp 316. Slide the pad or pads under the clamping bar 320 and move the screwdriver back to the center of the pan to close the clamp and lock the pads in place 324. Use the appropriate size bottle of sanitizing solution/chemical based on the number of pads in the sanitizing pan. For example, use 11.5 oz for one pad, 23 oz for two pads, 34.5 oz for three pads, 46 oz for four pads, 57.5 oz for five pads, and 69 oz for six pads. Pour the appropriate amount of sanitizing solution into the middle of the pads 328, allowing it to absorb through all the layers. The pads are now installed in the sanitizing pan and ready for use 332. Additional sanitizing chemical can be added to the absorbent pads if the pads are not worn out. Worn out or dried out pads can simply be removed and discarded.

Figure 11:
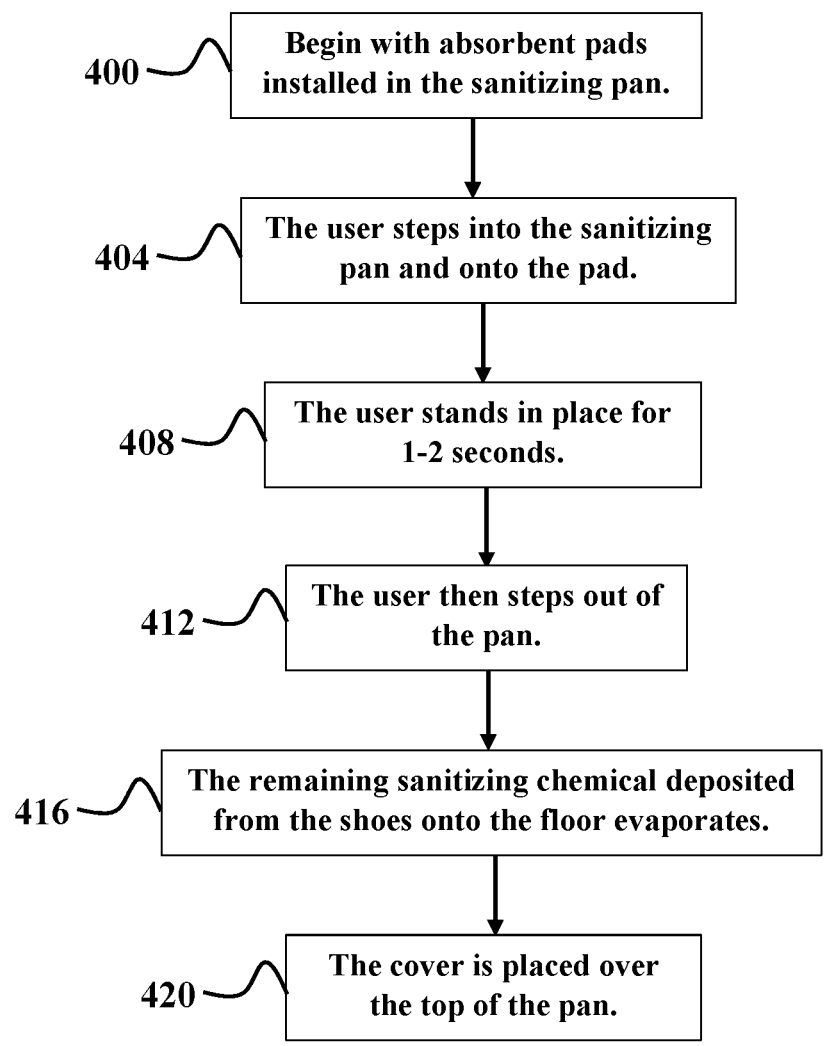
FIG. 11 is a flowchart showing the method of using the footwear sanitizing system.

FIG. 11 is a flowchart showing the method of using the footwear sanitizing system. Once the absorbent pads are installed in the sanitizing pan 400, the user simply steps into the sanitizing pan and onto the saturated pad 404. The user stands in place for 1-2 seconds 408 to allow the sanitizing chemical to wet the footwear. The user then steps out of the pan 412 and walks away. The remaining sanitizing chemical that is deposited from the shoe to the floor will evaporate quickly 416 leaving little to no moisture on the floor. When the system is not in use, the cover can be placed over the top of the pan 420 to reduce the evaporation rate of the sanitizing fluid.

Figure 12:
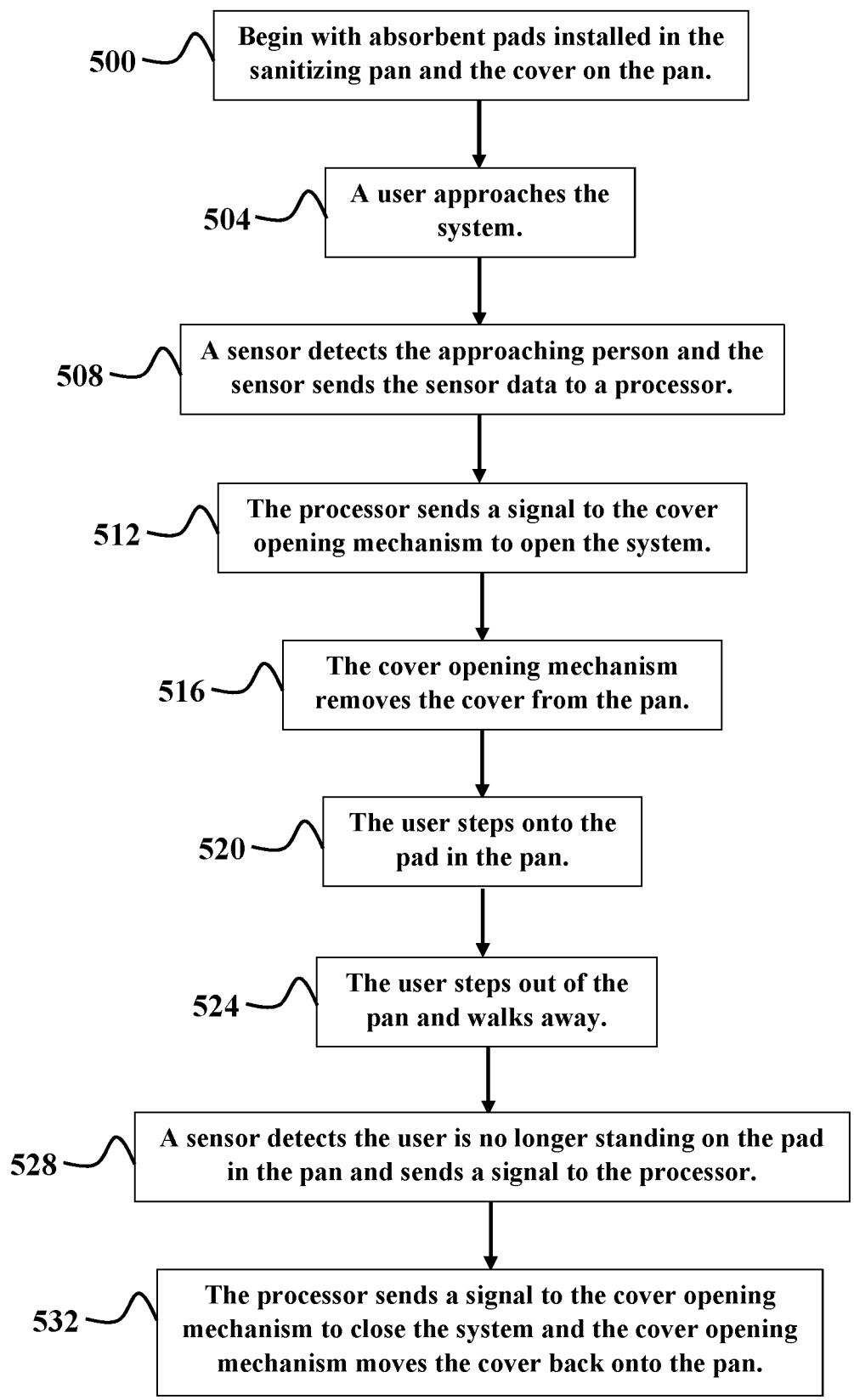
FIG. 12 is a flowchart showing the method of using a footwear sanitizing system with an automatic cover.

FIG. 12 is a flowchart showing the method of using a footwear sanitizing system with an automatic cover. The method begins with the absorbent pads installed in the sanitizing pan and the cover positioned on the pan 500. A user approaches the system 504. A sensor detects the approaching person 508. Any sensor can be used, as discussed above. The sensor sends the sensor data to a processor. The processor sends a signal to the cover opening mechanism to open the system by removing the cover 512. The cover opening mechanism removes the cover from the pan 516. The user steps onto the pad in the pan 520 and the sanitizing chemical is deposited onto the soles of the user's shoes. The user steps out of the pan and walks away 524. A sensor (which may be the same sensor or a different sensor than the first sensor that detected the person approaching) detects the user is no longer standing on the pad in the pan and sends a signal to the processor 528. The processor sends a signal to the cover opening mechanism to close the system and the cover opening mechanism moves the cover back onto the pan 532.

Figure 13:
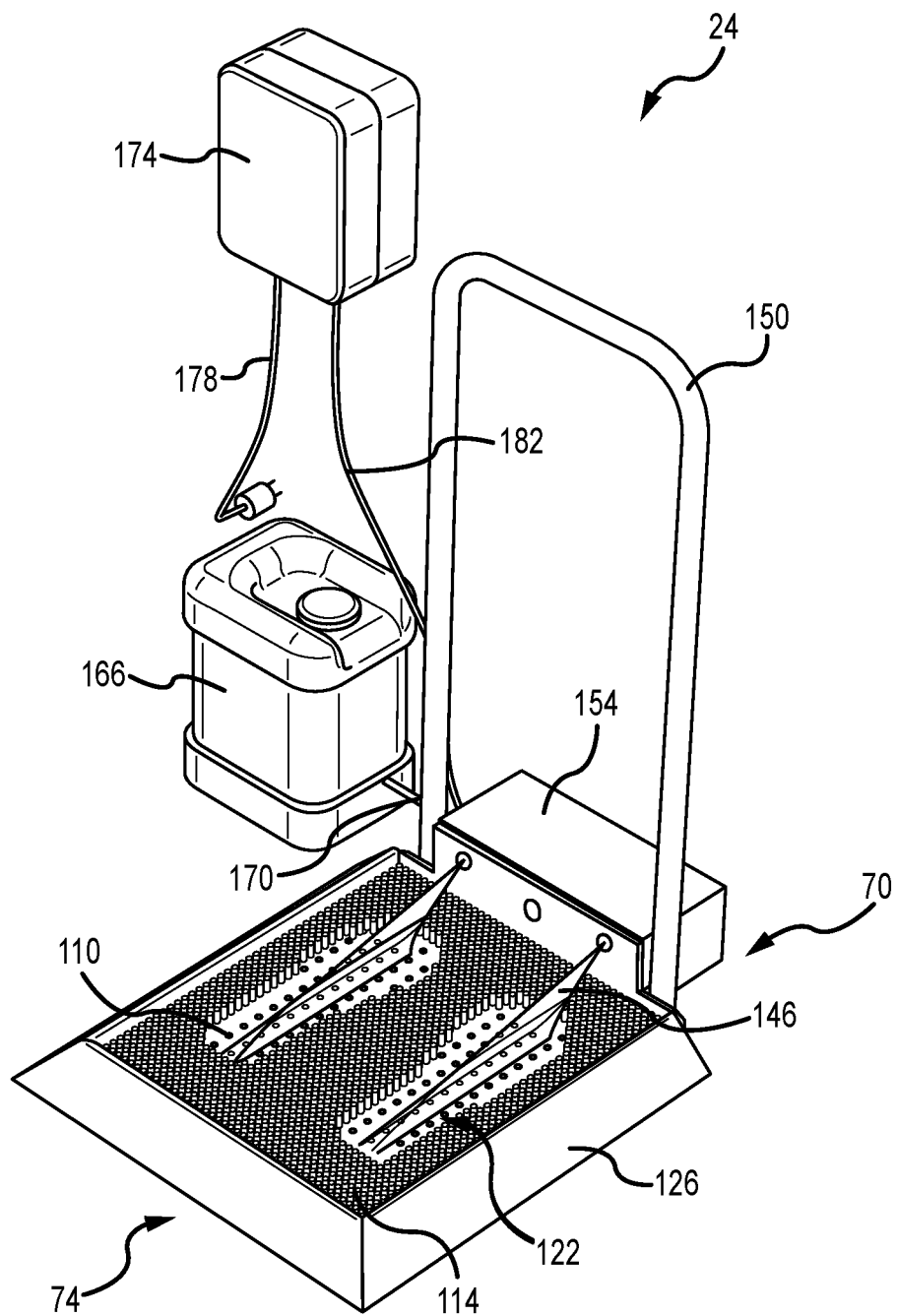
FIG. 13 is a perspective view of an alternative embodiment of a footwear sanitizing system.

Regarding FIG. 13, an alternative embodiment of a footwear sanitizing system 24 is shown. The footwear sanitizing system 24 comprises a pan 126 holding a plurality of mats 110, 114, a handrail 150, a pump housing 154 interconnected to a sanitizing solution container 166 via a fluid line 170, and a control box 174 having a power chord 178 and interconnected to the pump housing 154 via a control line 182.

Typically, the pan 126 is placed directly on the floor. However, the pan 126 can be placed in any desired location, including on a mat or other surface. The pan 126 may be shaped similar to the pan (item 26) described above with FIGS. 1-8. Alternatively, the pan 126 may be shaped differently. For example, the pan 126 may be oval-shaped, square, a rounded rectangle, or any other preferred shape. In the embodiment shown, the mats 110, 114 are rectangular shaped and fit in the rectangular-shaped pan 126. However, in other embodiments the mats 110, 114 may have different shapes such as round, oval, circular, square, or any other shape. In some embodiments, the mats 110, 114 are between about 10 inches and about 25 inches wide. In a typical embodiment, the mats 110, 114 are between about 14 inches and about 20 inches wide. More typically, the mats 110, 114 are about 17.75 inches wide. In some embodiments, the mats 110, 114 are between about 10 inches and about 30 inches long (measured from front to rear or toe to heel). In a typical embodiment, the mats 110, 114 are between about 16 inches and about 25 inches long. More typically, the mats 110, 114 are about 20.75 inches long.

In some embodiments, the system comprises two or more mats 110, 114. The first mat 114 is the top mat, which can be a heavy mat with cutouts 122 for the shoe area. The second mat (or middle mat) 110 can be the absorbent mat 110 with the sanitizing chemical and the mat on which the user actually stands. The second mat 110 is positioned below the first mat 114. The third mat is optional (not shown in FIG. 13, see FIG. 15) and is positioned below the second mat 110.

The second mat 110 is made of a resilient absorbent material that allows the sprayed sanitizing chemical 146 to quickly absorb and disperse across the mat 110. The absorbent mat 110 can be replaced as it wears from use. Alternatively, the absorbent mat 110 may be a disposable mat as described above in connection with the alternative embodiment (system 20 or 22). Because the absorbent second mat 110 must hold the sanitizing solution and deposit the solution onto the soles of a user's shoes when the user steps on the absorbent second mat 110, the absorbent second mat 110 must be absorbent. The absorbent second mat 110 may be sponge-like to permit the sanitizing liquid to move through the absorbent second mat 110 when the user steps on the mat. The absorbent second mat 110 may contain a negative charge to help attract "dipolar" water or other molecules in the sanitizing solution and absorb them. Additionally or alternatively, the absorbent second mat 110 may be comprised of fibers that have papillary action, meaning the fibers draw or suck in the liquid sanitizer like a straw through the interior of the fiber. The liquid is then stored in the interior cell walls until it eventually dries out or evaporates. The absorbent second mat 110 may be the same material or a similar material and have the same properties or similar properties as the pads discussed above in connection with FIGS. 1-8.

Regarding the first mat 114, the cutouts 122 may be shoe-shaped, oval-shaped, rectangular, or any other shape. Alternatively, the top mat 114 may have one cutout for both feet rather than two cutouts 122 (one for each foot). These cutouts 122 form the shoe area and give the user a specific place to stand where the sanitizing chemical 146 has been sprayed. Alternatively, the cutouts can be smaller than the shoe(s) or foot of the user. In this configuration, plural cutouts are employed for each shoe of the user to ensure that ample sanitizing solution is dispensed on the shoe. The cutouts 122 also keep the sanitizing chemical concentrated within the shoe area because the weight of the first mat 114 pushes on the absorbent second mat 110 and prevents or limits sanitizing solution from spreading into the portion of the second mat 110 directly below the top mat 114. Further, the top mat 114 is also heavy enough to function as a mechanical retainer and keep the absorbent mat 110 positioned in place. The top mat 110 can be any material, but may be rubber, metal, ceramic, plastic, glass, or any other material.

In some embodiments, the cutouts 122 are between about 2.0 inches and about 7.0 inches wide. In a typical embodiment, the cutouts 122 are between about 3.0 inches and about 6.0 inches wide. More typically, the cutouts 122 are about 4.0 inches wide. In some embodiments, the cutouts 122 are between about 8.0 inches and about 20.0 inches long. In a typical embodiment, the cutouts 122 are between about 12.0 inches and about 18.0 inches long. More typically, the cutouts 122 are about 16.0 inches long.

In some embodiments, the second mat has a greater liquid absorbency, permeability, and/or porosity than the first mat. In other words, the second mat can retain a greater volume of liquid than the first mat. For example, the second mat can absorb at least about 50% more liquid (per mat volume or in total for the mat) than the first mat. In some embodiments, the second mat can absorb at least about 60% more liquid (per mat volume or in total for the mat) than the first mat. Typically, the second mat can absorb at least about 75% more liquid (per mat volume or in total for the mat) than the first mat. More typically, the second mat can absorb at least about 85% more liquid (per mat volume or in total for the mat) than the first mat. The amount of liquid absorbed is measured by volume or weight of the liquid absorbed.

In some embodiments, the first mat has a greater weight, rigidity, and/or density than the second mat. This ensures that liquid absorbed by the second mat is pushed towards the cutouts, thereby ensuring greater cleaning and sanitizing of the user's footwear and minimizing wasted sanitizing solution. For example, the first mat is at least about 50% heavier (by weight) than the second mat. In some embodiments, the first mat is at least about 75% heavier (by weight) than the second mat. Typically, the first mat is at least about 100% heavier (by weight) than the second mat. Typically, the first mat is at least about 3 times heavier (by weight) than the second mat. More typically, the first mat is at least about 5 times heavier (by weight) than the second mat, meaning that the first mat weighs about 5 times the weight of the second mat. Additionally, in some embodiments, the first mat is at least about 50% more dense than the second mat. Typically, the first mat is at least about twice as dense (i.e., two times as dense) as the second mat. Typically, the first mat is at least about 3 times as dense as the second mat. More typically, the first mat is at least about 5 times as dense as the second mat. Moreover, in some embodiments, the first mat is at least twice as rigid as the second mat. Typically, the first mat is at least 3 times as rigid as the second mat.

In the embodiment shown, a pump housing 154 is interconnected to or positioned proximate the front 70 of the system 24 or front 70 of the pan 126. The pump housing 154 comprises the pump for spraying the sanitizing solution 146 onto the mat 110. The pump draws sanitizing solution from the sanitizing solution container 166 via the fluid line 170. The pump is controlled by the control box 174 and is in communication with the control box 174 via a control line 182. The control box 174 draws power from a power source via the power chord 178. The control box 174 may also supply power to the pump via the control line 182. The control box 174 may comprise a prime button to prime the system 24 by spraying sanitizing solution while the prime button is pressed, a solution capacitive sensor to detect solution, and a solution empty indicator light to indicate when the sanitizing solution container 166 is empty.

A handrail 150 may be interconnected to the pan 126 or the floor and is provided for the safety and comfort of the users. A user can hold onto the handrail 150 as he/she steps into and out of the pan 126.

Figure 14:
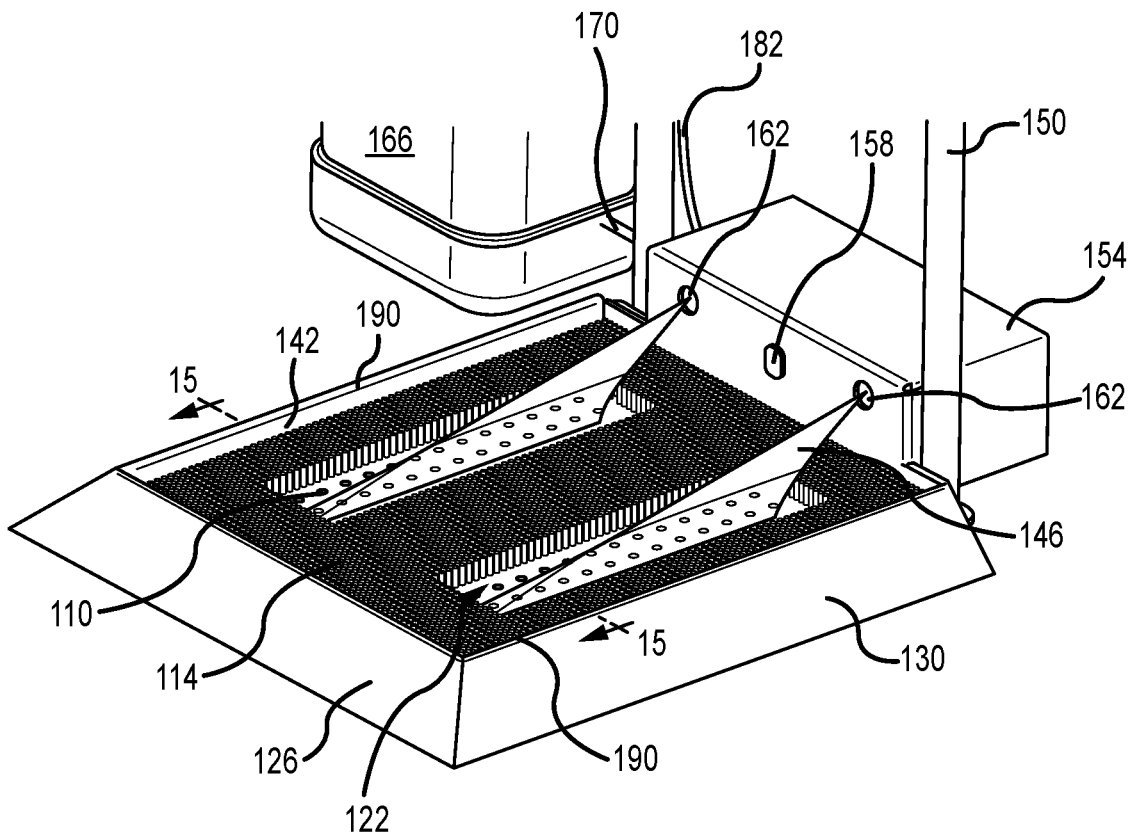
FIG. 14 is perspective view of a portion of the footwear sanitizing system.

FIG. 14 is perspective view of a portion of the footwear sanitizing system 24. The system comprises a pan 126 for holding two or more mats 110, 114. Here the top mat 114 has rectangular cutouts rather than shoe-shaped cutouts 122. The pan 126 has outer sides 130, inner sides (also called "inner sidewalls" herein) 142, and an upper edge 190 positioned between and interconnecting the outer sides 130 and inner sides 142.

The pump housing 154 is interconnected to or positioned proximate the pan 126. The pump housing 154 comprises the pump for spraying the sanitizing solution 146 onto the mat 110. The pump draws sanitizing solution from the sanitizing solution container 166 via the fluid line 170 and sprays the sanitizing solution 146 out of the pump housing 154 and onto the absorbent mat 110 via one or more nozzles 162. The nozzles 162 may be stainless steel or any other material. The pump is in communication with the control box and receives power via a control line 182. The pump housing 154 also comprises a sensor 158 to sense an approaching user. The sensor 158 can be any sensor, including those described above in connection with FIGS. 4A, 4B, and 5. In one embodiment, the sensor 158 is a photoelectric eye. After the sensor 158 senses an approaching user, the pump will spray sanitizing solution 146 onto at least a portion of the shoe areas 122. In some embodiments, the sanitizing solution 146 is sprayed in a flat, longitudinal pattern at least a portion of the length of a cutout 122, i.e., the shoe area. The sanitizing solution then spreads out across the width of the shoe area 122 via wicking and absorption. In alternative embodiments, the nozzles 162 rotate to spray the flat, longitudinal spray pattern 146 across the width of the cutouts or shoe areas 122. In other embodiments, the system comprises more than one nozzle 162 per cutout 122 such that two or more straight, flat streams are sprayed onto each cutout 122. In a typical embodiment, the pump housing comprises three nozzles 162 per cutout 122 and each nozzle 162 sprays a straight stream 146 onto the absorbent mat 110 within the cutout 122. Each stream 146 is sprayed about 1 inch apart from the other stream 146. In another embodiment, the pump housing 154 comprises one nozzle 162 per cutout 122 and the nozzle 162 sprays one straight stream 146, then rotates or slides to the left or right and sprays a second straight stream 146 about 1 inch away from the first stream 146, and then rotates or slides again to spray a third straight stream about 1 inch away from the second stream 146. In still another embodiment, the nozzles 162 may spray a jet-like stream onto a single point on the absorbent mat 110. Then the sanitizing solution spreads out on the absorbent mat 110 to cover a majority or all of the shoe area 122. In additional embodiments, the nozzles spraying the jet-like streams may rotate or move to spray the jet-like streams onto multiple different points within the shoe area 122. Still further, the system may have multiple nozzles spraying jet-like streams on multiple different points of each shoe area 122.

The system 24 has multiple independent electronic controls that control the sensor 158, solution pump, prime button, solution empty indicator light, and solution capacitive sensor. To add additional sanitizing chemical to the mat 110, a user can press a prime button on the control panel, and sanitizing chemical will be sprayed onto the mat 110 until the button is released. If the sanitizing solution container 166 is empty, a red indicator light on the control panel will light up. To replace the sanitizing solution, the user will replace the sanitizing solution container 166 with a new container and press and hold the prime button until the red indicator is no longer illuminated and the sanitizing solution is spraying 146 from the nozzles 162.

Figure 15:
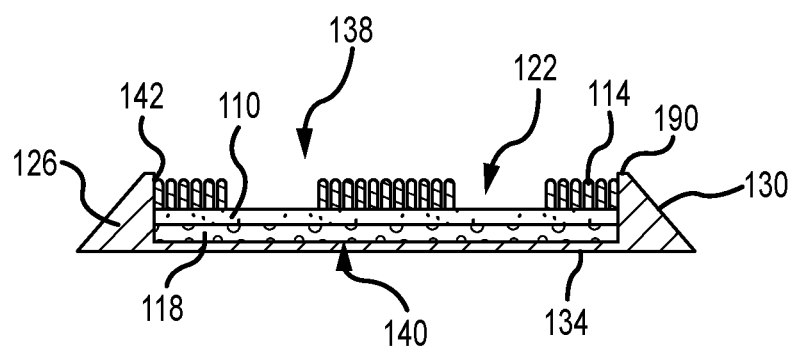
FIG. 15 is a cross-sectional view of the footwear sanitizing system taken at line 15-15 of FIG. 14.

FIG. 15 is a cross-sectional view of the footwear sanitizing system taken at line 15-15 of FIG. 14. In the embodiment shown, the pan 126 is rectangular shaped and includes four outer sides 130, a bottom 134, and a cavity 138 formed by multiple inner sides 142 and a bottom surface 140. The bottom 134 may have an abrasive surface, rubber, or other coating or layer to prevent slipping on a flat, smooth floor. Alternatively, the pan 126 may be bolted to the floor or secured to the floor in another known manner. The four outer sides 130 extend upwardly from the bottom 134. The inner sides 142 extend upwardly from the bottom surface 140 of the cavity. The bottom 134 is positioned on the floor; thus, the bottom 134 is substantially flat. For example, in one embodiment, the outer sides 130 of the pan 126 are positioned at an angle between about 30° and about 75° as measured from the bottom 134 of the pan 126. In a typical embodiment, the outer sides 130 of the pan 126 are positioned at an angle between about 40° and about 60° as measured from the bottom 134 of the pan 126. The outer sides 130 may be sloped (as shown) or vertical and substantially perpendicular to one another. The outer sides 130 terminate in a substantially flat (horizontal or angled inward) edge 190. The upper edge 190 may be curved, substantially flat, substantially horizontal, or angled in other embodiments. The upper edge 190 is positioned between and connects the outer sides 130 and the inner sides 142. The pan 126 has a cavity 138 for holding the mats 110, 114, 118. The inner sides 142 and bottom surface 140 form the cavity 138 and the inner sides 142 may be substantially vertical (as shown) or may slope inward or outward. Here, the inner sides 142 are substantially straight to align with the substantially straight sides of the mats 110, 114, 118. Alternatively, the inner sides 142 may be curved or another shape to match the shape of the mats 110, 114, 118. The cavity 138 may be approximately the same shape and size of the mats 110, 114, 118 for securely holding the mats 110, 114, 118. The bottom surface 140 of the cavity 138 is substantially flat and substantially parallel to the bottom 134 of the pan 126.

The pan 126 may be composed of a metal material, plastic material, composite material, acrylic material, ceramic material, glass, glass-like material, or other sturdy material that does not absorb moisture and prevents the transmission or evaporation of liquid and that does not react with the sanitizing chemical. Thus, any material can be used, but preferred characteristics of the pan material include strength (the material should be strong and not break or fracture if kicked or stepped on), little to no absorption of liquid (the liquid in the pads should stay in the pads and not be soaked up by the pan), limit the transmission of the liquid out of the pan (to prevent and limit evaporation of the sanitizing chemical), and not degrade due to constant contact with the sanitizing chemical.

The pan 126 may also have a liner, film, or coating along the cavity 138 (including the bottom 140 of the cavity and the inner sidewalls 142) to protect the pan 126 from the chemicals used in the sanitizing solution, i.e., to prevent the pan 126 from degrading or reacting with the chemicals used in the sanitizing solution.

The three mats 110, 114, 118 are clearly shown in FIG. 15. The top mat 114 has cutouts 122 forming the shoe areas. The absorbent second mat 110 is positioned below the top mat 114. The third mat 118 is positioned below the second mat 110. The third mat is for cushion and variations in conforming to various sole tread patterns. In some embodiments, the third mat 118 is a bubble mat. A domed rubber mat that allows for cushion and variation in conforming to various sole tread patterns.

The mats 110, 114, 118 can vary in thickness depending on the specific use, size, and sanitizing chemical used. For example, the top mat 114 may be between about 0.0625 inch and about 1.5 inch thick. Typically, the top mat 114 is between about 0.125 inch and about 1.0 inch thick. More typically, the top mat 114 is about 0.5 inch thick. The absorbent second mat 110 may be between about 0.05 inch and about 1.0 inch thick. Typically, the absorbent second mat 110 is between about 0.0625 inch and about 0.5 inch thick. More typically, the absorbent second mat 110 is about 0.125 inch thick. The third mat 118 may be between about 0.125 inch and about 1.0 inch thick. Typically, the third mat 118 is between about 0.25 inch and about 0.75 inch thick. More typically, the third mat 118 is about 0.375 inch thick.

Desired characteristics of the top mat 114 include the desired absorbency, texture, density, weight, flexibility, traction, and durability. For example, typically the top mat 114 is non-absorbent. Typically the top mat 114 has a smooth texture.

The typical density of the top mat 114 is between about 25 lb/ft$^3$ and about 490 lb/ft$^3$. A more typical density of the top mat 114 is about 69 lb/ft$^3$. The typical weight of the top mat 114 is between about 0.5 lb and about 6.0 lb. A more typical weight of the top mat 114 is about 1.69 lb.

Desired characteristics of the absorbent second mat 110 include the desired absorbency, texture, abrasive upper surface, density, weight, backing, and thickness. For example, the typical absorbency of the absorbent second mat 110 is between about 100 mL/ft$^2$ and about 250 mL/ft$^2$. A more typical absorbency of the absorbent second mat 110 is about 164 mL/ft$^2$. A more typical absorbency of the absorbent second mat 110 is about 410 mL per pad. The porosity of the absorbent second mat 110 is also important as the pores/channels can also absorb and/or transport the liquid sanitizer. Thus, the number of pores/capillaries/channels per square inch and the size thereof also affects the absorption rate and qualities of the absorbent second mat 110.

The typical texture of the absorbent second mat 110 is mildly abrasive. In some embodiments, it may be desirable for the upper surface of the absorbent second mat 110 (the surface that touches the sole of the user's shoes) to have an abrasive texture such that the user does not slip on the mat and to increase the amount and rate the sanitizer transfers to the user's shoe soles. Alternatively, a smooth upper surface may be desired such that the user's shoes do not stick to and rip the absorbent second mat 110. The typical abrasiveness of the upper surface of the absorbent second mat 110 is fibrous.

The typical density of the absorbent second mat 110 is between light weight and medium weight, for example between about 5.0 lb/ft$^3$ and about 15.0 lb/ft$^3$ (about 80 kg/m$^3$ and about 240 kg/m$^3$). A more typical density of the absorbent second mat 110 is a medium weight density, for example about 11.0 lb/ft$^3$ (about 176 kg/m$^3$).

The weight of the absorbent second mat 110 and material used therein can affect the amount of sanitizer solution that can be absorbed and how quickly the liquid solution spreads (wicking time (seconds) or level (measured in cm or inches)) throughout the absorbent second mat 110. The typical weight of the absorbent second mat 110 is about 0.10 lb and about 1.5. A more typical weight of the absorbent second mat 110 is 0.29 lb.

The absorbent mats may be comprised of multiple materials and layers. In some embodiments, the absorbent second mat 110 is comprised of felt material. In other embodiments, the absorbent second mat 110 can be comprised of cotton, polyester, cellulose, polypropylene, and other durable materials. The absorbent second mat 110 may comprise cellulose to make the mat absorbent. The absorbent second mat 110 may be comprised of natural and/or synthetic materials. Further, the absorbent second mat 110 may include gels, crystals, or beads that absorb moisture, such as Super Absorbent Polymer (SAP) or Absorbent Gel Material (AGM).

Desired characteristics of the third mat 118 include the desired absorbency, density, weight, flexibility, traction, and durability. For example, typically the third mat 118 is non-absorbent.

The typical density of the third mat 118 is between about 25 lb/ft$^3$ and about 150 lb/ft$^3$. A more typical density of the third mat 118 is between about 50 lb/ft$^3$ and about 100 lb/ft$^3$. A more typical density of the third mat 118 is about 69 lb/ft$^3$. The typical weight of the third mat 118 is between about 1.0 lb and 6.0 lb. A more typical weight of the third mat 118 is about 4.0 lb.

The third mat 118 may be comprised of multiple materials and layers. In some embodiments, the third mat 118 is comprised of a rubber material. In other embodiments, the third mat 118 can be comprised of rubber, nylon, silicone, EPDM, Neoprene, and/or other materials. The third mat 118 may comprise cellulose to make the mat absorbent. The third mat 118 may be comprised of natural and/or synthetic materials. Further, the third mat 118 may include gels, crystals, or beads that absorb moisture, such as Super Absorbent Polymer (SAP) or Absorbent Gel Material (AGM).

Figure 16:
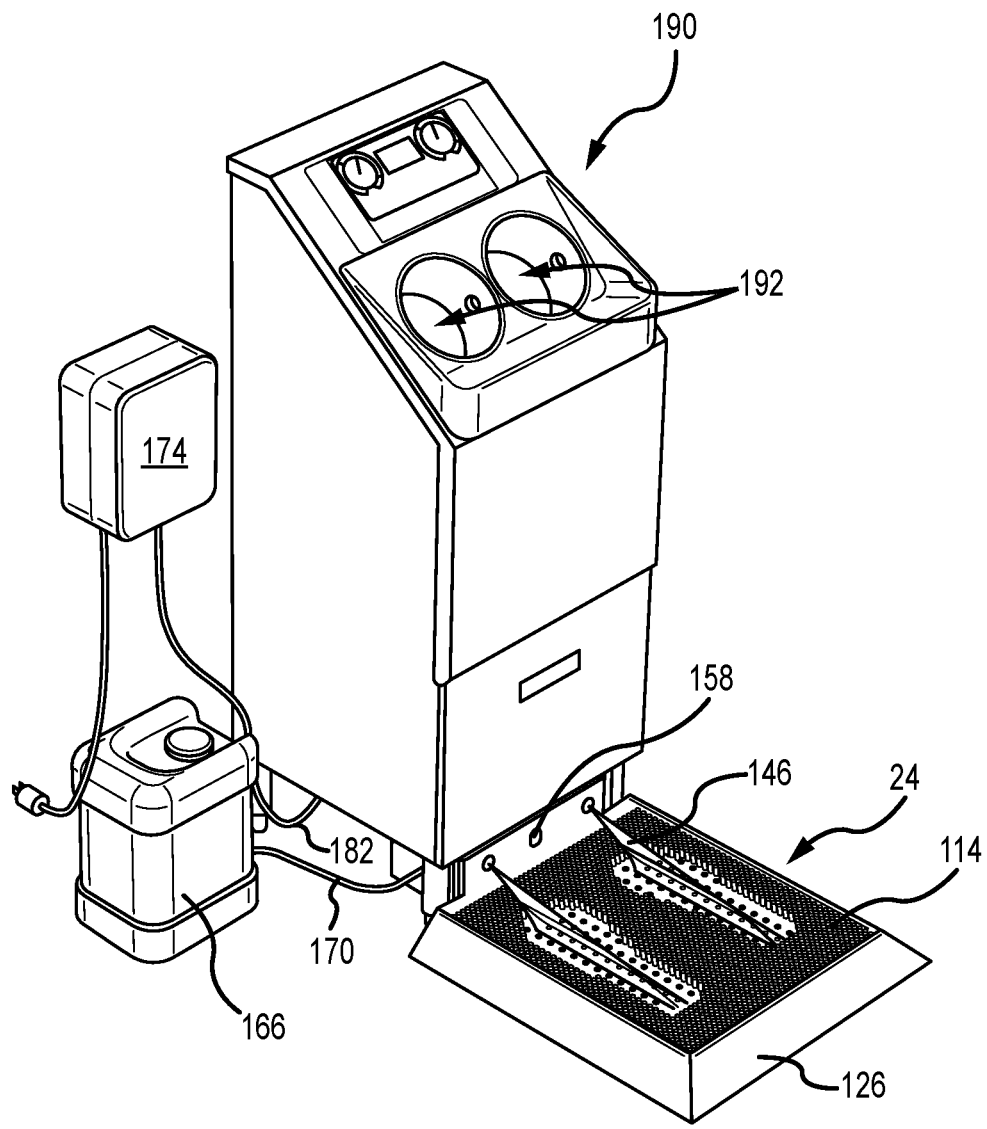
FIG. 16 is a perspective view of a footwear sanitizing system interconnected to an automatic handwashing station.

FIG. 16 is a perspective view of a footwear sanitizing system 24 interconnected to an automatic handwashing station 190. The footwear sanitizing system 24 is sized and shaped to interconnect to an automatic handwashing station 190. Thus, the user can wash her hands at the same time her footwear is sanitized.

The embodiments shown in FIGS. 13-16 may also include a cover similar to the cover shown and described with FIGS. 4A-5. The cover may be manually operated or automatically operated as described above.

Figure 17:
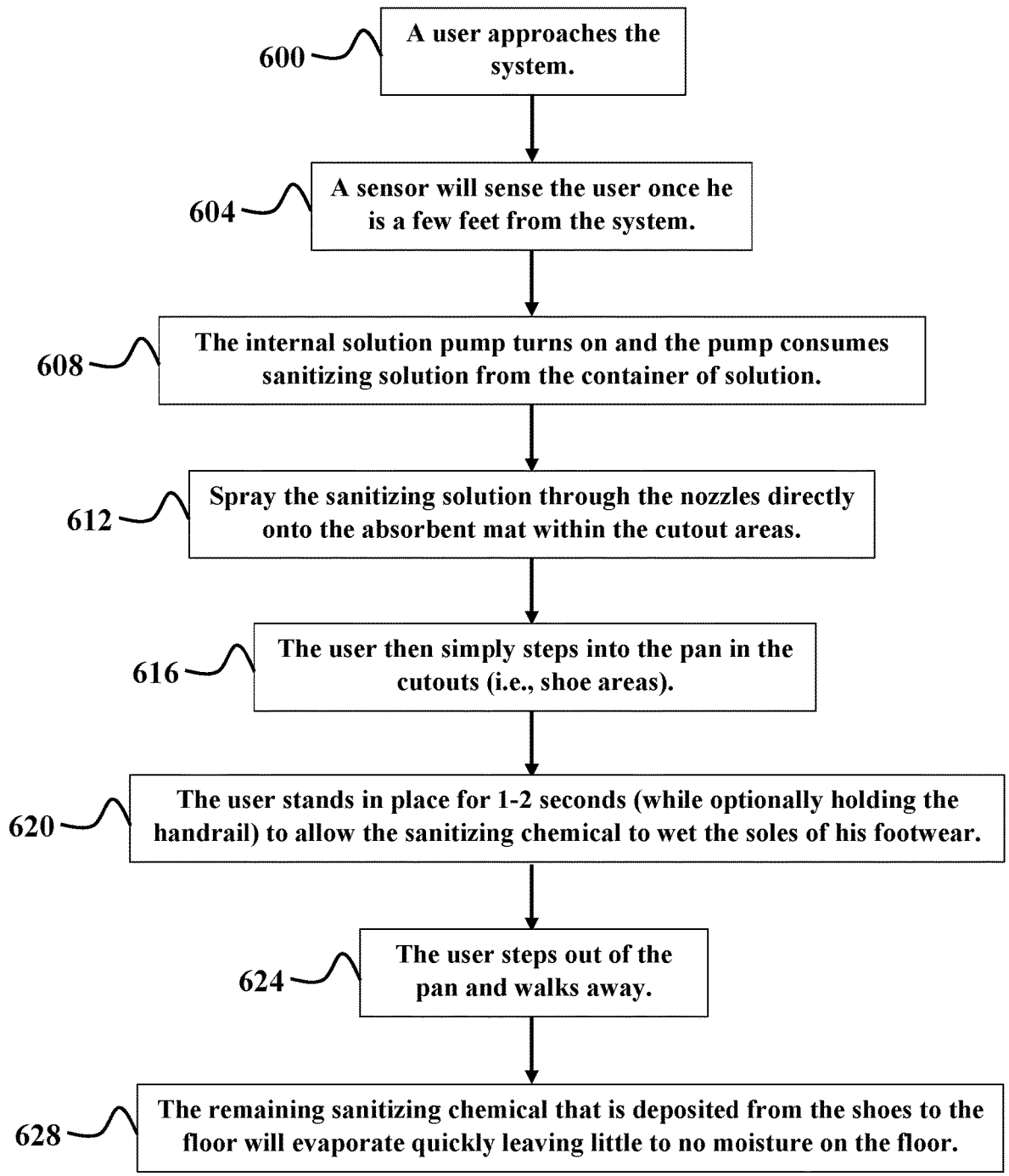
FIG. 17 is a flowchart showing the method of using the footwear sanitizing system.

Regarding FIG. 17, as a user approaches the system 600, a sensor (e.g., a photoelectric eye) will sense the user once he is a few feet (e.g., approximately 2-3 feet) from the system 604. The internal solution pump will turn on, consuming sanitizing solution from the container of solution 608, and the system will spray the sanitizing solution through two nozzles directly onto the mat within the two shoe-shaped or rectangular areas 612. In one embodiment, the system will spray for approximately 0.5 seconds to 3.0 seconds and will use between about 2.0 mL and about 8.0 mL of sanitizing solution, depending on the exact chemical used and the requirements of the system, which are determined by the operator or user. If additional sanitizer is needed, press and hold the prime button until the desired mat saturation level is reached. In some embodiments, the sanitizing solution is sprayed in a flat, longitudinal pattern the length of a cutout area, i.e., the shoe area. In other embodiments, the sanitizing solution is sprayed in jet-like streams onto the absorbent mat. The user then simply steps into the pan in the cutouts (i.e., shoe areas) 616 while holding the handrail for safety and stands in place for 1-2 seconds to allow the sanitizing chemical to wet the soles of his footwear 620. The user then steps out of the pan and walks away. The remaining sanitizing chemical that is deposited from the shoes to the floor will evaporate quickly leaving little to no moisture on the floor.

The initial setup for the footwear sanitizing system comprises the following steps: place the pan in the desired location, e.g., in front of an automated handwasher; route the ⅜" tube with the quick connector from the stand under the handwasher and attach it to the pan manifold; and place the three mats into the pan, ensuring that they are in the correct order from bottom to top: black bubble mat, grey absorptive mat (with soft side up), red foot placement mat (with grip knobs upward). Place the sanitizer solution container into the basket attached to the stand; connect the pickup tube cap to the sanitizer bottle, and connect the yellow cable coming out the back of the handwasher to the electrical connection on the front of the stand. Power is now connected to the system, and the red "Footwear Solution Empty" light should illuminate. Press and hold the prime button for approximately 30 seconds or until the desired mat saturation level is reached. The "Footwear Solution Empty" light should now be off, and the system is ready for use.

To clean and maintain the pan and mats, drain and clean the pan at least once per day when is use. If excessive pooling occurs in the pan, or if the mat becomes regularly undersaturated during use, adjust the sanitizer dispensation. To clean the system remove mats from the pan and clean the mats by hosing them down to remove soil. Let the mats air dry. Clean and sanitize the pan completely, including the underside of the pan. Once the mats are dry and the pan is clean, re-install the mats. Put the base mat (which may be black) in the pan first, then put the absorbent felt mat in the pan, and last put the heavy mat with cutouts (which may be red) in the pan on top of the absorbent mat. Follow the instructions for initial startup to refill the system.

In various embodiments, the sanitizing chemical is a mixture of isopropyl alcohol and quaternary ammoniums. In some embodiments, the absorbent pads and absorbent mats consist of mostly isopropyl alcohol. The sanitizing solution may also include water in addition to the alcohol and ammonium. In one embodiment, the percentage of isopropyl alcohol in the solution is between about 30% and about 70%. Typically, the percentage of isopropyl alcohol in the solution is between about 40% and about 60%. More typically, the percentage of isopropyl alcohol in the solution is about 50%. In some embodiments, the percentage of quaternary ammoniums (also called "quats") in the solution is between about 0.001% and about 5%. More typically, the percentage of quaternary ammoniums in the solution is about 0.01%. In some embodiments, the percentage of dimethlbenzyl ammonium chloride in the solution is between about 0.001% and about 1.0%. Typically, the percentage of dimethlbenzyl ammonium chloride in the solution is about 0.01%. In some embodiments, the percentage of dimethyl ethylbenzyl ammonium chlorides in the solution is between about 0.001% and about 1.0%. Typically, the percentage of dimethyl ethylbenzyl ammonium chlorides in the solution is about 0.01%. In some embodiments, the percentage of the other ingredients (including water) in the solution is between about 25% and about 75%. Typically, the percentage of the other ingredients (including water) in the solution is between about 40% and about 60%. More typically, the percentage of the other ingredients (including water) in the solution is about 49.9%.

Rubbing alcohol, hand sanitizer, and disinfecting pads typically contain a 60-70% solution of isopropyl alcohol in water. Water is required to open up membrane pores of bacteria, which acts as a gateway for isopropyl alcohol. A 75% v/v solution in water may be used as a hand sanitizer. Isopropyl alcohol is used as a water-drying aid. Isopropyl alcohol dissolves a wide range of non-polar compounds. It also evaporates quickly, leaves nearly zero oil traces, compared to ethanol, and is relatively non-toxic, compared to alternative solvents. Isopropyl alcohol is miscible in water, ethanol, ether, and chloroform. It will dissolve ethyl cellulose, polyvinyl butyral, many oils, alkaloids, gums and natural resins. Isopropyl alcohol is not miscible with salt solutions and can be separated from aqueous solutions by adding a salt such as sodium chloride.

Quaternary ammonium cations, also known as quats, are typically positively charged polyatomic ions of the structure $NR^+_4$, R being an alkyl group or an aryl group. Unlike the ammonium ion ($NH^+_4$) and the primary, secondary, or tertiary ammonium cations, the quaternary ammonium cations are typically permanently charged, independent of the pH of their solution. Quaternary ammonium salts or quaternary ammonium compounds (called quaternary amines in oilfield parlance) are typical salts of quaternary ammonium cations.

Quaternary ammonium salts are used as disinfectants, surfactants, fabric softeners, and as antistatic agents (e.g., in shampoos). Quaternary ammonium compounds have also been shown to have antimicrobial activity. Certain quaternary ammonium compounds, especially those containing long alkyl chains, are used as antimicrobials and disinfectants. Examples are benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide. Also good against fungi, amoebas, and enveloped viruses, quaternary ammonium compounds are believed to act by disrupting the cell membrane. Quaternary ammonium compounds are lethal to a wide variety of organisms except endospores, Mycobacterium tuberculosis, and non-enveloped viruses.

The sanitizing solution can be added to the pads or mats at room temperature. Alternatively, the sanitizing solution can be heated and added to the mats or pads at some temperature above room temperature.

The sanitizing solution is removed from the user's shoes via both physical motion (i.e., being shaken off of the user's shoes) and volatility (i.e., evaporating). In some embodiment, at least about 50% of the sanitizing solution will volatize within about 5 seconds from the user's shoes after the user steps out of the sanitizing pan and off of the sanitizing pad or mat. In some embodiment, at least about 50% of the sanitizing solution will volatize within about 3 seconds from the user's shoes after the user steps out of the sanitizing pan and off of the sanitizing pad or mat. In some embodiment, at least about 50% of the sanitizing solution will volatize within about 2 seconds from the user's shoes after the user steps out of the sanitizing pan and off of the sanitizing pad or mat. In some embodiment, at least about 50% of the sanitizing solution will volatize within about 1 second from the user's shoes after the user steps out of the sanitizing pan and off of the sanitizing pad or mat. In some embodiment, at least about 75% of the sanitizing solution will volatize within about 5 seconds from the user's shoes after the user steps out of the sanitizing pan and off of the sanitizing pad or mat. In some embodiment, at least about 75% of the sanitizing solution will volatize within about 3 seconds from the user's shoes after the user steps out of the sanitizing pan and off of the sanitizing pad or mat.

In some embodiment, at least about 50% of the sanitizing solution will volatize within about 5 seconds, when deposited on the floor from the user's shoes. In some embodiment, at least about 50% of the sanitizing solution will volatize within about 3 seconds, when deposited on the floor from the user's shoes. In some embodiment, at least about 50% of the sanitizing solution will volatize within about 2 seconds, when deposited on the floor from the user's shoes. In some embodiment, at least about 50% of the sanitizing solution will volatize within about 1 second, when deposited on the floor from the user's shoes. In some embodiment, at least about 75% of the sanitizing solution will volatize within about 5 seconds, when deposited on the floor from the user's shoes. In some embodiment, at least about 75% of the sanitizing solution will volatize within about 3 seconds, when deposited on the floor from the user's shoes.

In some embodiments, the sanitizing solution has a vapor pressure of at least about 5 mm Hg at 0° C. Typically, the sanitizing solution has a vapor pressure of at least about 7.5 mm Hg at 0° C. More typically, the sanitizing solution has a vapor pressure of at least about 10 mm Hg at 0° C.

Any portions of the embodiments shown in FIGS. 1-8 can be used in combination with or as alternatives to any portions of the embodiments shown in FIGS. 13-16, and vice versa. The features of one embodiment can be used with features of other embodiments. Additionally, the methods of FIGS. 9-12 can be used when any embodiment described herein.

While various embodiments of the present invention have been described in detail, it is apparent that modifications and alterations of those embodiments will occur to those skilled in the art. However, it is to be expressly understood that such modifications and alterations are within the scope and spirit of the present invention, as set forth in the following claims. Further, the invention(s) described herein is capable of other embodiments and of being practiced or of being carried out in various ways. It is to be understood that the phraseology and terminology used herein is for the purpose of description and should not be regarded as limiting.

A number of variations and modifications of the invention can be used. It would be possible to provide for some features of the invention without providing others. The present invention, in various embodiments, configurations, or aspects, includes components, methods, processes, systems and/or apparatus substantially as depicted and described herein, including various embodiments, configurations, aspects, subcombinations, and subsets thereof. Those of skill in the art will understand how to make and use the present invention after understanding the present disclosure. The present invention, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments, configurations, or aspects for the purpose of streamlining the disclosure. The features of the embodiments, configurations, or aspects of the invention may be combined in alternate embodiments, configurations, or aspects other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the invention.

Moreover, though the description of the invention has included description of one or more embodiments, configurations, or aspects and certain variations and modifications, other variations, combinations, and modifications are within the scope of the invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The invention claimed is:

1. A footwear sanitizing system comprising:
a pan with a bottom positioned on a floor and a cavity opening to an upper side of the pan opposite the bottom;
a second mat positioned in the pan;
a first mat positioned on top of the second mat within the cavity, wherein the first mat has at least one cutout extending through the first mat to the second mat such that the second mat is accessible through the at least one cutout in the first mat, wherein at least one of a liquid absorbency, permeability, and porosity of the second mat is greater than the first mat;
a pump housing interconnected to the pan, the pump housing comprising a sensor, at least one nozzle, and a pump;
a controller electrically interconnected to the pump and the sensor; and
a fluid container in fluid communication with the pump, wherein the fluid container contains a sanitizing solution, and wherein the pump is in fluid communication with the at least one nozzle,
wherein the at least one cutout comprises at least first and second cutouts sized to receive footwear of a user, wherein a weight of the first mat is heavier than a weight of the second mat, wherein the at least one nozzle comprises at least first and second nozzles, each of the first and second nozzles being spatially proximate to a corresponding one of the first and second cutouts, and wherein the fast-drying sanitizing solution is sprayed out of the first nozzle in a substantially flat, longitudinal pattern at least half a length of the first cutout and the sanitizing solution is sprayed out of the second nozzle in a substantially flat, longitudinal pattern at least half a length of the second cutout.

2. The footwear sanitizing system of claim 1, further comprising a cover for covering the pan, wherein the cover engages with the pan to enclose the second mat from an outside environment.

3. The footwear sanitizing system of claim 1, wherein the pan comprises:
four outer sidewalls extending upwardly from the bottom of the pan and forming a pan perimeter;
a substantially flat bottom surface of the cavity, wherein the bottom surface is substantially parallel to the bottom of the pan;
four inner sidewalls extending upwardly from the bottom surface of the cavity and forming a cavity perimeter of the cavity; and
an upper edge positioned between and interconnecting the four inner sidewalls to the four outer sidewalls.

4. The footwear sanitizing system of claim 3, wherein the four outer sidewalls are positioned at an angle greater than about 30 degrees as measured from the bottom of the pan, and wherein the four inner sidewalls are substantially perpendicular to the bottom surface of the cavity.

5. The footwear sanitizing system of claim 3, wherein the cavity perimeter is substantially concentric with the pan perimeter.

6. The footwear sanitizing system of claim 3, wherein the upper edge is substantially flat and substantially parallel to the bottom of the pan.

7. The footwear sanitizing system of claim 3, further comprising a cover for covering the pan, wherein the cover engages with the upper edge of the pan to enclose the mats from an outside environment.

8. The footwear sanitizing system of claim 3, wherein the second mat and the first mat are sized and shaped to fit in the cavity of the pan.

9. The footwear sanitizing system of claim 1, wherein the first mat is at least about twice as dense as the second mat when the second mat is substantially dry.

10. The footwear sanitizing system of claim 1, wherein the cavity is formed by a substantially flat bottom surface that is substantially parallel to the bottom of the pan and inner sidewalls extending upwardly from the bottom surface.

11. The footwear sanitizing system of claim 1, further comprising at least one liner, film, or coating positioned on at least a bottom surface of the cavity.

12. The footwear sanitizing system of claim 1, wherein the sanitizing solution is fast-drying and wherein the fast-drying sanitizing solution comprises isopropyl alcohol and quaternary ammoniums.

13. The footwear sanitizing system of claim 1, wherein the pan is comprised of a substantially non-porous material that inhibits the transmission of moisture, and wherein the second mat is comprised of a substantially porous and permeable material that adsorbs the sanitizing solution.

14. The footwear sanitizing system of claim 2, further comprising a handrail interconnected to the pan or the floor, wherein the handrail is positioned in a front portion of the system, wherein the cover automatically opens and closes in response to a signal from the controller, and wherein, in a first mode, the controller receives a first signal from the sensor indicating the presence of a user at a first spatial location and opens the cover and, in a second mode, the controller receives a second signal from the sensor indicating the presence of the user at a second spatial location and closes the cover.

15. The footwear sanitizing system of claim 1, wherein the sensor is one or more of a photoelectric eye, a motion detector, an optical sensor, and a pressure sensor.

16. The footwear sanitizing system of claim 1, wherein the at least one cutout has a rectangular shape, shoe shape, or oval shape.

17. A method of sanitizing footwear, comprising
providing a pan with a bottom and a cavity that is open to a top opposite the bottom;
providing a first mat in the cavity;
providing a second mat in the cavity, wherein the first mat has a greater liquid absorbency, porosity, or permeability than the second mat and the second mat has a greater weight or rigidity than the first mat;
placing the second mat directly on top of the first mat, wherein the second mat has a first cutout and a second cutout sized to receive footwear of a user such that the first mat is accessible through the first and second cutouts, wherein the first and second mats are sized and shaped to fit in the cavity of the pan, and wherein a weight of the second mat is heavier than a weight of the first mat;
providing a first nozzle and positioning it spatially proximate to the first cutout;
providing a second nozzle and positioning it spatially proximate to the second cutout;
providing a first sensor for receiving sensor data, including detecting an approaching user;
sending the sensor data to a processor in a controller, including data regarding the approaching user;
sending a signal to the pump instructing the pump to suction a sanitizing solution from a container;
spraying the sanitizing solution out of the first nozzle and onto the first mat within the first cutout of the second mat in a substantially flat, longitudinal pattern at least half a length of the first cutout for about 1 to about 5 seconds;
spraying the sanitizing solution out of the second nozzle and onto the first mat within the second cutout of the second mat in a substantially flat, longitudinal pattern at least half a length of the second cutout for about 1 to about 5 seconds;
sensing the user standing on the first mat via the first sensor;
not spraying the sanitizing solution while the user is standing on the first absorbent mat; and
sensing that the user no longer is standing on the first mat via the first sensor.

18. A footwear sanitizing system comprising:
a pan with a bottom positioned on a floor and a cavity opening to an upper side of the pan opposite the bottom;
a second mat positioned in the pan;
a first mat positioned on top of the second mat within the cavity, wherein the first mat has at least one cutout extending through the first mat to the second mat such that the second mat is accessible through the at least one cutout in the first mat, wherein at least one of a liquid absorbency, permeability, and porosity of the second mat is greater than the first mat;
a pump housing interconnected to the pan, the pump housing comprising a sensor, at least one nozzle, and a pump;
a controller electrically interconnected to the pump and sensor;
a fluid container in fluid communication with the pump, wherein the fluid container contains a sanitizing solution, and wherein the pump is in fluid communication with the at least one nozzle;
a cover for covering the pan, wherein the cover engages with the pan to enclose the second mat from an outside environment; and
a handrail interconnected to the pan or the floor, wherein the handrail is positioned in a front portion of the system, wherein the cover automatically opens and closes in response to a signal from the controller, and wherein, in a first mode, the controller receives a first signal from the sensor indicating the presence of a user at a first spatial location and opens the cover and, in a second mode, the controller receives a second signal from the sensor indicating the presence of the user at a second spatial location and closes the cover.

* * * * *